United States Patent [19]
Anderson et al.

[11] Patent Number: 5,385,732
[45] Date of Patent: Jan. 31, 1995

[54] VARIANTS OF TISSUE PLASMINOGEN ACTIVATOR, COMPOSITIONS AND METHODS OF USE FOR SAME

[75] Inventors: Stephen Anderson, Princeton, N.J.; Kevin M. Brady, Concord, Calif.; Bruce A. Keyt, Pacifica, Calif.; Leonard G. Presta, San Francisco, Calif.

[73] Assignee: Genentech, Inc., South San Francisco, Calif.

[21] Appl. No.: 35,427

[22] Filed: Mar. 22, 1993

Related U.S. Application Data

[63] Continuation of Ser. No. 824,740, Jan. 21, 1992, Pat. No. 5,270,198, which is a continuation of Ser. No. 480,691, Feb. 15, 1990, abandoned, which is a continuation-in-part of Ser. No. 196,909, May 20, 1988, abandoned.

[51] Int. Cl.$^6$ ................ C12N 9/48; A61K 32/547
[52] U.S. Cl. ...................... 424/94.64; 424/94.63; 435/226
[58] Field of Search ............ 435/212, 219, 226; 424/94.63, 94.64

[56] References Cited

U.S. PATENT DOCUMENTS

| | | | |
|---|---|---|---|
| 4,766,075 | 8/1988 | Goeddel et al. | 435/240.2 |
| 5,041,376 | 8/1991 | Gething et al. | 435/172.3 |

FOREIGN PATENT DOCUMENTS

| | | |
|---|---|---|
| 93619 | 11/1983 | European Pat. Off. |
| 207589 | 1/1987 | European Pat. Off. |
| 225286 | 6/1987 | European Pat. Off. |
| 227462 | 7/1987 | European Pat. Off. |
| 231624 | 8/1987 | European Pat. Off. |
| 238304 | 9/1987 | European Pat. Off. |
| 240334 | 10/1987 | European Pat. Off. |
| 241208 | 10/1987 | European Pat. Off. |
| 241209 | 10/1987 | European Pat. Off. |
| 242836 | 10/1987 | European Pat. Off. |
| 253241 | 1/1988 | European Pat. Off. |
| 266032 | 5/1988 | European Pat. Off. |
| 352904 | 1/1990 | European Pat. Off. |
| 370205 | 5/1990 | European Pat. Off. |
| WO84/01960 | 5/1984 | WIPO |
| WO86/01538 | 3/1986 | WIPO |
| WO8704722 | 8/1987 | WIPO |
| WO8912681 | 12/1989 | WIPO |

OTHER PUBLICATIONS

Gunzler, W. et al., "The Primary Structure of High Molecular Mass Urokinas from Human Urine The Complete Amino Acid Sequence of the A Chain," *Hoppe-Seyler's Z. Physiol. Chem. Bd.* 363: S. 1155–1165 (1982).

Holmes, W., et al., "Cloning and Expression of the Gene for Pro–Urokinase in Escherichia Coli," *Bio/Technology* 3: 923–929 (1985).

Kasai, S. et al., "Proteolytic Cleavage of Single-chain Pro–urokinase Induces Conformational Change which Follows Activation of the Zymogen and Reduction of Its High Affinity for Fibrin," *J. Biol. Chem.* 260(22): 12377–12381 (1985).

Kasai, S. et al., "Thrombolytic Properties of an Inactive Proenzyme Form of Human Urokinase Secreted from Human Kidney Cells," *Cell Structure and Function* 10: 151–159 (1985).

(List continued on next page.)

*Primary Examiner*—Garnette D. Draper
*Assistant Examiner*—Marianne Porta Allen
*Attorney, Agent, or Firm*—Ginger R. Dreger

[57] ABSTRACT

A fibrinolytically active amino acid sequence variant of a plasminogen activator is prepared that has one or more glycosylation sites in regions that are not glycosylated in the native molecule. DNA sequences can be prepared that encode the variants, as well as expression vectors incorporating the DNA sequences, and host cells transformed with the expression vectors. The variants may be used in a pharmaceutical preparation to treat a vascular disease or condition in patients.

26 Claims, 12 Drawing Sheets

OTHER PUBLICATIONS

Pennica, D. et al., "Cloning and Expression of Human Tissue-type Plasminogen Activator cDNA in E. coli," *Nature* 301: 214–221 (1983).

Rijken and Collen, "Purification and Characterization of the Plasminogen Activator Secreted by Human Melanoma Cells in Culture," *J. Biol. Chem.* 256(13): 7035–7041 (1981).

Steffens, G. et al., "The Complete Amino Acid Sequence of Low Molecular Mass Urokinas from Human Urine," *Hoppe-Seyler's Z. Physiol. Chem. Bd.* 363: S. 1043–1058 (1982).

Pharmacia Fine Chemicals Catalogue 84, pp. 1 and 6.

Kaufman et al., Gene Amplification, 245–250, Cold Spring Harbor Laboratory (1982).

Ny et al., DNA, 7(10): 671–677 (1988).

Rickles et al., J. Biol. Chem., 263(3): 1563–1569 (1988).

Gardell et al., J. Biol. Chem., 264(30): 17947–17952 (1989).

Machamer & Rose, J. Biol. Chem., 263(12): 5948–5954 (1988).

Machamer & Rose, J. Biol. Chem., 263(12): 5955–5960 (1988).

Browne et al., J. Biol. Chem., 263(4): 1599–1602 (1988).

Harris, Protein Engineering, 1(6): 449–458 (1987).

Berman & Lasky, Trends in Biotechn. 3(2): 51–53 (1985).

N-LINKED GLYCOSYLATION OF PROTEINS

— MAMMALIAN CELLS —

"COMPLEX"    "SIMPLE"

— YEAST —

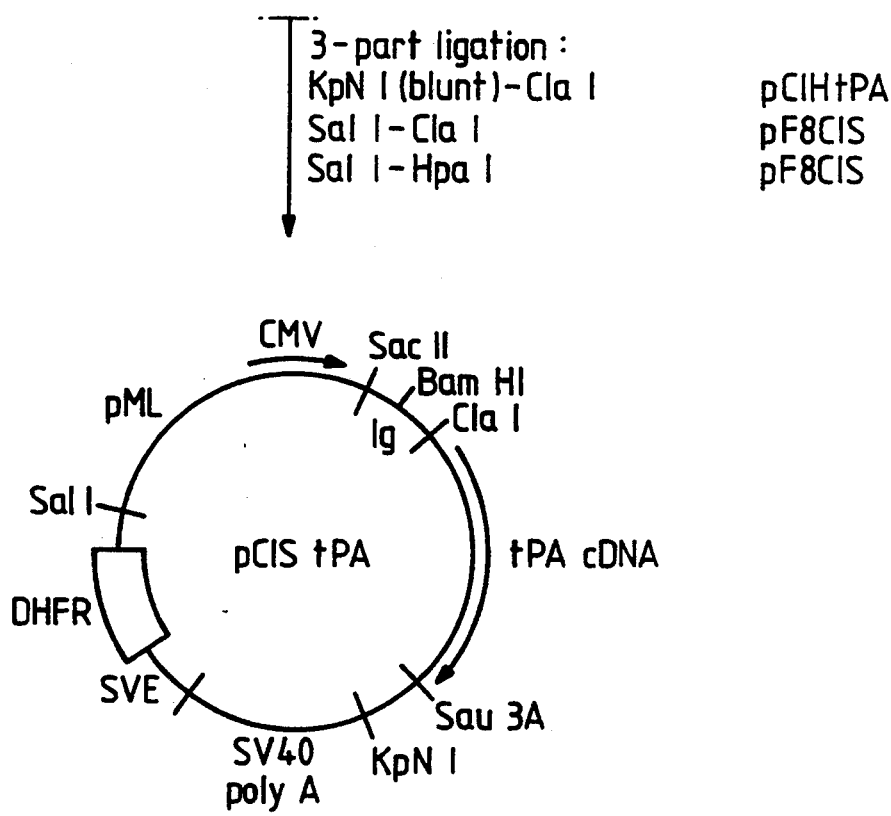

TIME (MIN.)

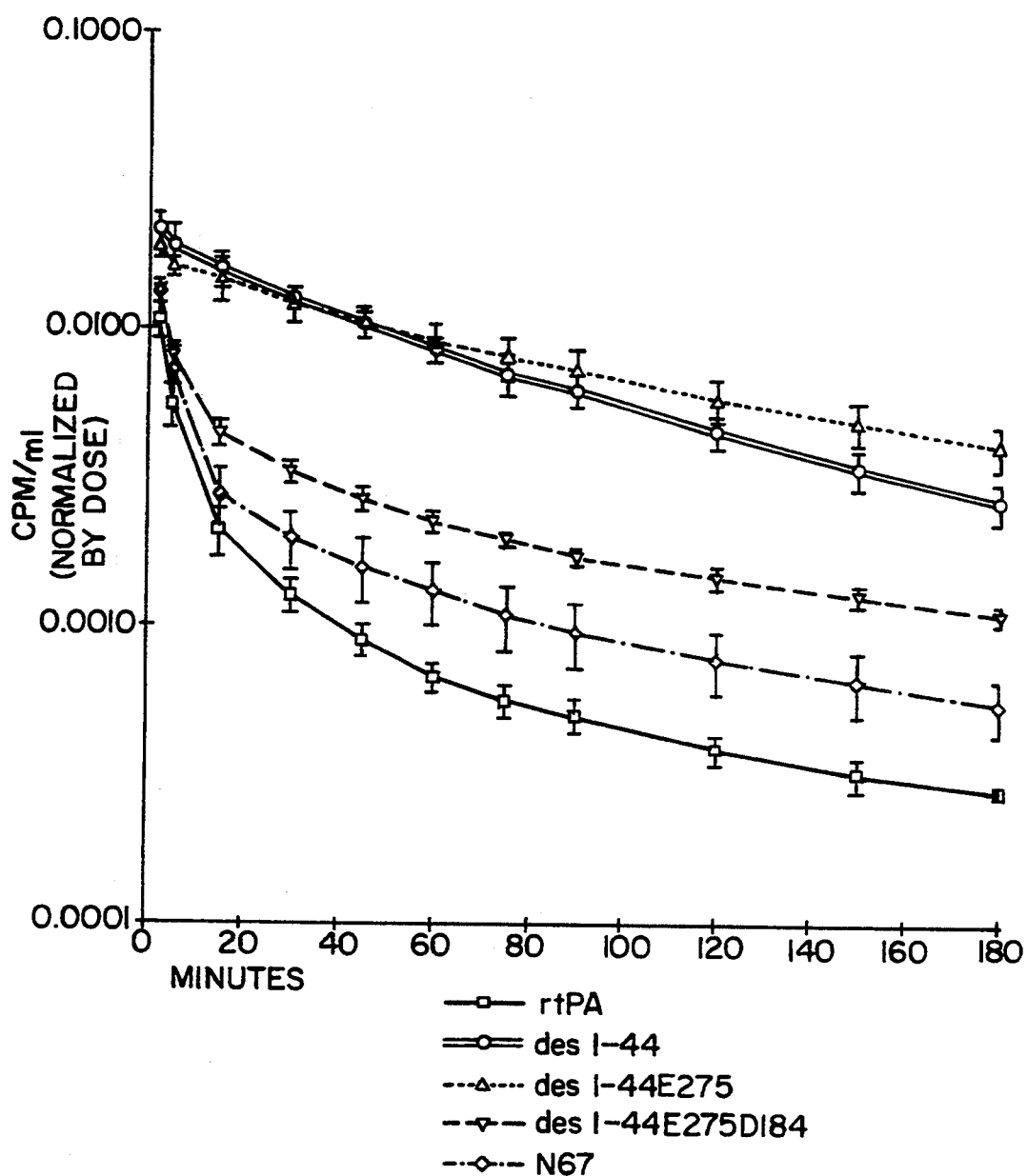

VARIANTS OF TISSUE PLASMINOGEN ACTIVATOR, COMPOSITIONS AND METHODS OF USE FOR SAME

CROSS-REFERENCE TO RELATED APPLICATIONS

This application is a continuation application of copending U.S. Ser. No. 07/824,740 filed Jan. 21, 1992, now U.S. Pat. No. 5,270,198 which is a continuation application of U.S. Ser. No. 07/480,691 filed Feb. 15, 1990, now abandoned, which is a continuation-in-part application of U.S. Ser. No. 07/196,909 filed May 20, 1988, now abandoned.

BACKGROUND OF THE INVENTION

1. Field of the Invention

The present invention is directed to particular variants of plasminogen activators, to methods for preparing such, and to methods and compositions utilizing such variants for producing pharmaceutically active compositions with unexpectedly improved therapeutic and physicochemical characteristics, particularly longer circulating half-life and slower clearance rates.

2. Description of Background and Related Art

Plasminogen activators are enzymes that activate the zymogen plasminogen to generate the serine proteinase plasmin (by cleavage at Arg560-Val561) that degrades various proteins, including fibrin. Among the plasminogen activators studied are streptokinase, a bacterial protein, urokinase, an enzyme synthesized in the kidney and elsewhere and originally extracted from urine, and human tissue plasminogen activator (t-PA), an enzyme produced by the cells lining blood vessel walls.

The mechanism of action of each of these plasminogen activators differs: Streptokinase forms a complex with plasminogen, generating plasmin activity, urokinase cleaves plasminogen directly, and t-PA forms a ternary complex with fibrin and plasminogen, leading to plasminogen activation in the locality of the clot.

t-PA has been identified and described as a particularly important and potent new biological pharmaceutical agent that has shown extraordinary results in the treatment of vascular diseases, such as myocardial infarction, due to its high fibrin specificity and potent ability to dissolve blood clots in vivo.

t-PA has been the subject of numerous scientific and patent application disclosures. Although its existence prompted numerous investigations by several scientific groups, it was first identified as a substantially pure isolate from a natural source, and tested for requisite plasminogen activator activity in vivo, by Collen et al., European Patent Application Publn. No. 41,766, published Dec. 16, 1981, based upon a first filing of Jun. 11, 1980. See also the corresponding scientific publication, Rijken et al., *J. Biol. Chem.*, 256: 7035 (1981).

Subsequently, t-PA was fully identified and characterized by underlying DNA sequence and deduced amino acid sequence based on successful work employing recombinant DNA technology resulting in large quantities of t-PA in a distinct milieu. This work was reported by Pennica et al., *Nature*, 301:214 (1983)) and in European Patent Application Publn. No. 93,619, published Nov. 9, 1983, based upon a first filing of May 5, 1982.

Using the latter disclosure as a basic tool, numerous other researchers have reported on the thus enabled preparation of the molecule via recombinant DNA technology. Certain of these researchers also have disclosed publicly the potential of variants of the basic structure, mentally foreseeing derivatives that may vary in overall biological or pharmacokinetic effects. The resultant public disclosures for the most part have been prophetic and equivocal in terms of actual overall biological or pharmacological results.

Analogous endeavors in the laboratories that succeeded first in producing t-PA recombinantly have been recorded factually in terms of confirmed molecular characterization and observed biological effect, both in the scientific literature and in various patent applications. In all events, the trend seems to favor research attempting to modify the basic structure of t-PA to explore and exploit fully its commercial potential according to various biologically based endpoints.

Based partly upon such research and disclosures, it seems now clear that the t-PA molecule contains five domains (stretches of amino acid sequence) that have been defined with reference to homologous or otherwise similar structures identified in various other proteins such as trypsin, chymotrypsin, plasminogen, prothrombin, fibronectin, and epidermal growth factor (EGF). These domains have been designated, starting at the N-terminus of the amino acid sequence of t-PA, as 1) the finger region (F) that has variously been defined as including amino acids 1 to about 44, 2) the growth factor region (G) that has been variously defined as stretching from about amino acids 45 to 91 (based upon its homology with EGF), 3) kringle one (K1) that has been defined as stretching from about amino acid 92 to about amino acid 173, 4) kringle two (K2) that has been defined as stretching from about amino acid 180 to about amino acid 261, and 5) the so-called serine protease domain (P) that generally has been defined as stretching from about amino acid 264 to the C-terminal end of the molecule. These domains are situated generally adjacent to one another, or are separated by short "linker" regions, and account for the entire amino acid sequence of from 1 to 527 amino acids of the putative mature form of t-PA.

Each domain has been described variously as contributing certain specific activity. The finger domain has been variously described as containing a sequence of at least major importance for high binding affinity to fibrin. (This activity is thought important for the high specificity that t-PA displays with respect to clot lysis at the locus of a fibrin-rich thrombus.) The growth factor-like region likewise has been associated with cell surface binding activity, at least with respect to urokinase. The kringle 2 region has also been strongly associated with fibrin binding and with the ability of fibrin to stimulate the activity of t-PA. The serine protease domain is responsible for the plasminogen activating activity of t-PA.

Potential N-linked glycosylation sites exist in the molecule at amino acid positions 117, 184, 218, and 448, numbered in accordance with native, mature t-PA. The site at amino acid 218 is not glycosylated in native t-PA. The glycosylation site at amino acid 117 has been characterized as being a high mannose type, while the other two sites display so-called complex oligosaccharide structures. Sites 117 and 448 seem always to be glycosylated, when the molecule is derived from a host cell capable of effecting glycosylation, while site 184 is thought to be glycosylated in about 50 percent of the molecules.

The glycosylated/unglycosylated phenomenon at site 184 has been demonstrated via SDS-PAGE analysis, where two bands can be seen, one associated with glycosylated molecules at position 184, and the other unglycosylated molecules at position 184. These bands have been designated as Type I and Type II t-PA, respectively. This partial glycosylation pattern may be the result of site 184 being situated in a conformationally sheltered position in the protein. For a more detailed discussion of the glycosylation structures of t-PA, see copending U.S. Ser. No. 07/118,098, filed Nov. 6, 1987, now abandoned, and its parent applications.

Another locus of scientific note is the so-called proteolytic cleavage site within the region defined by amino acids 275 to about 279, and more particularly, the bond between amino acid 275 and 276 of the native molecule. See U.S. Ser. No. 07/071,506, filed Jul. 9, 1987, now abandoned, and its parent applications. Mutagenesis at this site so as to make it less susceptible to proteolytic degradation creates a molecule that remains in a single-, or one-chain, form that is thought to have certain advantages biologically and commercially.

As mentioned above, another plasminogen activator, urokinase, has been purified from human urine and human kidney cell culture fluids (Gunzler et al., *Hoppe-Seyler's Z. Physiol. Chem.*, 363: 1155–1165 (1982) and Steffens, et al., *Hoppe Seyler's .Z. Physiol. Chem.*, 363: 1043–1058 (1982)) and produced recombinantly (EPO Publ. No. 154,272 and Holmes et al., *Biotechnology*, 3: 923–929 (1985)).

Urokinase contains 411 amino acids and is produced with an N-terminal leader sequence that is cleaved during maturation, resulting in the production of prourokinase. Prourokinase is in turn cleaved by plasmin to yield two urokinase species: one of molecular weight 54,000 daltons and one of molecular weight 33,000 daltons.

Urokinase has three identifiable domains: a growth factor domain encompassing positions 5 to 49, a kringle domain embracing positions 50 to 136, and a serine protease domain encompassing positions 159 to 411. Prourokinase similarly consists of these three domains. See Gunzler et al., supra. The enzymatically active amino acid residues in urokinase have been located at positions 204, 255, and 356, and an N-linked glycosylation site occurs at Asn302.

When used in large doses, urokinase results in degradation and activation of coagulation and fibrinolysis factors that leads to bleeding. In .contrast, the precursor form of human urokinase, prourokinase, described in EPO Publ. No. 139,447 and in *J. Biol. Chem.*, 260: 12377 (1985), dissolves thrombi without inducing any substantial bleeding. *Cell Struc. Func.*, 10:151 (1985).

A review article on plasminogen activators and second-generation derivatives thereof is Harris, *Protein Engineering*, 1: 449–458 (1987).

Natural t-PA has a plasma half-life of typically about six minutes or less, when administered to patients in therapeutically effective amounts. Prourokinase has a similar half-life. Such a half-life is desirable under certain situations, for example, when acute aggressive therapy of a life-threatening disease such as myocardial infarction or pulmonary embolism is undertaken. In this high-risk situation, patients may be treated who have significant or unrecognized potential for uncontrolled bleeding. If such bleeding occurred, drug administration could be stopped and the causative t-PA levels would be rapidly depleted by high clearance rates.

However, in other circumstances, for example, in the treatment of myocardial infarction following reperfusion, the desired therapeutic regimen is less aggressive and of extended duration (4 to 12 hours). A long half-life (or slower clearance rate) form of t-PA can be perceived as a more desirable, efficient and convenient treatment in patients who are not in life-threatening situations. Moreover, a t-PA of slower clearance rate would be desirable as an agent for bolus administration. For example, because ambulance technicians generally do not have infusion capability available, it would be much more desirable to employ t-PA-like agents having slower clearance rates.

All of the defined domains and glycosylation sites, and the one-chain/two-chain cleavage site of t-PA have been described as having specific potential biological activity components. For example, removal of a substantial portion or all of the finger domain results in a molecule with substantially diminished fibrin binding characteristics, albeit in return there is a decrease in the overall rate of clearance of the resultant entity—see U.S. Ser. No. 07/068,448, filed Jun. 30, 1987, now abandoned, its continuation Ser. No. 07/188,237, now U.S. Pat. No. 4,935,237; and its continuation Ser. No. 07/539,987, now U.S. Pat. No. 5,037,646.

Modification of the native molecule so as to destroy the one-chain to two-chain cleavage site, as such, results in a molecule with somewhat altered biological activity and more stability while the fibrin binding and fibrin stimulation are increased relative to two-chain t-PA—see U.S. Ser. No. 07/071,506, supra.

The advantages of glycosylation of proteins for use as pharmaceuticals are provided by Berman and Lasky, *Trends in Biotechnology* "Engineering Glycoproteins for Use as Pharmaceuticals" (1985). However, deletion of glycosylation sites at positions 117–119, 184–186, and 448–450 of t-PA resulted in higher specific activity as the mole percent carbohydrate was reduced. See EPO Pub. No. 227,462. Further, the t-PA mutants with Asn119, Ala186 and Asn450, which have the N—glycosylation sites selectively removed by DNA modification but contain residual O—linked carbohydrate, were found to be about two-fold as potent as melanoma t-PA in an in vitro lysis assay. See EPO Publ. No. 225,286.

However, alteration of the glycosylation sites, and in particular that at amino acid 117, seems invariably to result in a molecule having affected solubility characteristics that may result additionally in an altered circulating half-life pattern and/or fibrin binding characteristics - see copending U.S. Ser. No. 07/118,098, supra.

When the growth factor domain of t-PA is deleted, the resultant mutant is still active and binds to fibrin, as reported by A. J. van Zonneveld et al., *Thrombos. Haemostas.*, 54 (1) 4 (1985). Various deletions in the growth factor domain have also been reported in the patent literature. See EPO Publ. No. 241,209 (des-51-87), EPO Publ. No. 241,208 (des-51-87 and des-51-173), PCT 87/04722 (deletion of all or part of the N-terminal 1-91), EPO Publ. No. 231,624 (all of growth factor domain deleted), and EPO Publ. No. 242,836 and Jap. Pat. Appl. Kokai No. 62-269688 (some or all of the .growth factor domain deleted). In addition, Gething et al. reported on Apr. 19, 1989 at the "Second International Workshop on the Molecular and Cellular Biology of Plasminogen Activation" meeting at Brookhaven National Laboratory, Long Island, N.Y., Apr. 17-21, 1989, that the t-PA variant with an asparagine at position 67 is expected to display a significantly longer circulatory half-life than wild-type t-PA.

It has further been shown that t-PA can be modified both in the region of the first kringle domain and in the growth factor domain, resulting in increased circulatory half-life and thus slower clearance rate). See EPO Pat. Publ. No. 241,208 published Oct. 14, 1987. The region between amino acids 51 and 87, inclusive, can be deleted from t-PA to result in a variant having slower clearance from plasma. Browne et al., *J. Biol. Chem.*, 263:1599–1602 (1988). Also, t-PA can be modified, without adverse biological effects, in the region of amino acids 67 to 69 of the mature, native t-PA, by deletion of certain amino acid residues or replacement of one or more amino acids with different amino acids. See EPO Pat. Publ. No. 240,334 published Oct. 7, 1987. Moreover, when the entire or a partial epidermal growth factor domain of the human prourokinase protein is deleted or replaced by one or more different amino acid residues, the resultant variants exhibit increased half-life in blood. See EPO Pat. Publn. No. 253,241 published Jan. 20, 1988.

There is a current and continuing need in the art to identify specific sites within plasminogen activator molecules that can be modified to impart to the molecules improved pharmacokinetic characteristics over the native molecule. Such variant molecules would provide medical science important new alternatives in the treatment of cardiovascular disease and numerous other medical conditions that arise from thromboembolic occlusion of blood vessels.

Accordingly, it is an object of this invention to provide plasminogen activator molecules to patients requiring clot-dissolving agents that exhibit improved therapeutic and pharmaceutical characteristics.

Another object is to provide plasminogen activator molecules with a longer half-life and slower clearance rate from plasma relative to that of currently available clot-dissolving agents.

It is another object to provide for the treatment of conditions that admit the use of clot-dissolving agents having longer circulatory half-lives and slower clearance rates from plasma relative to natural t-PA, for example, conditions such as deep vein thrombosis or peripheral arterial thrombosis (peripheral vascular disease).

These and other objects will be apparent to one of ordinary skill in the art.

SUMMARY OF THE INVENTION

These objects are achieved by the provision of a plasminogen activator amino acid sequence variant that exhibits fibrinolytic activity and contains one or more glycosylation sites at regions that are not glycosylated in the corresponding native plasminogen activator.

In one preferred embodiment, such glycosylation is at a site containing a Asn-X-Ser or Asn-X-Thr tripeptidyl sequence of the variant, wherein X is any amino acid except proline.

In another embodiment, the plasminogen activator is glycosylated within its finger, growth factor or kringle 1 domain.

In still another embodiment, the plasminogen activator is t-PA, and the tyrosine residue at position 67, numbered in accordance with the native amino acid sequence of t-PA, is substituted with another amino acid capable of glycosylation, such as asparagine, serine, or threonine, preferably asparagine.

In still another embodiment, the plasminogen activator is t-PA, and the residue at position 50 or 103, numbered in accordance with the native amino acid sequence of t-PA, is substituted with an asparagine residue.

In still another embodiment, the plasminogen activator is t-PA, and the residue at position 39 or 60, numbered in accordance with the native amino acid sequence of t-PA, is substituted with a serine residue.

In other embodiments, this invention relates to a DNA sequence encoding the variant described above, replicable expression vectors capable of expressing the DNA sequence in a transformant host cell, and microorganisms and cell cultures transformed with the vector.

In yet another embodiment, the invention is directed to a composition for treating a vascular disease or condition comprising a therapeutically effective amount of the variant herein in admixture with a pharmaceutically acceptable carrier.

In still another embodiment, the invention provides a method of treating a vascular disease or condition in a patient comprising administering the above composition containing the variant to the patient.

The present invention is based, inter alia, upon specific successful research demonstrating that glycosylation at a site of the plasminogen activator that is not ordinarily glycosylated in the native molecule results in variants that have an extended circulatory half-life and slower clearance rate as compared with the native material. The results are molecules that differ substantially from the native material in overall amino acid sequence, but exhibit pharmacokinetic properties to a degree permitting their commercialization in conjunction with or as an alternative to the native material.

BRIEF DESCRIPTION OF THE DRAWINGS

FIGS. 4a, 4b, 5a and 5b are schematic representations of a suitable method for the preparation of pCISt-PA, together with a description of certain of its prominent restriction sites.

FIG. 10 shows the pharmacokinetic profiles, in rabbits, of rt-PA, des (1–44) t-PA, des 1–44E275 t-PA, des 1–44E275D184, and glycosylated N67 t-PA, all except N67 t-PA expressed in stable CHO cell lines. The N67 material was obtained via transient expression in 293 cells.

DETAILED DESCRIPTION OF THE PREFERRED EMBODIMENTS

A. Definitions

Figure 1A:
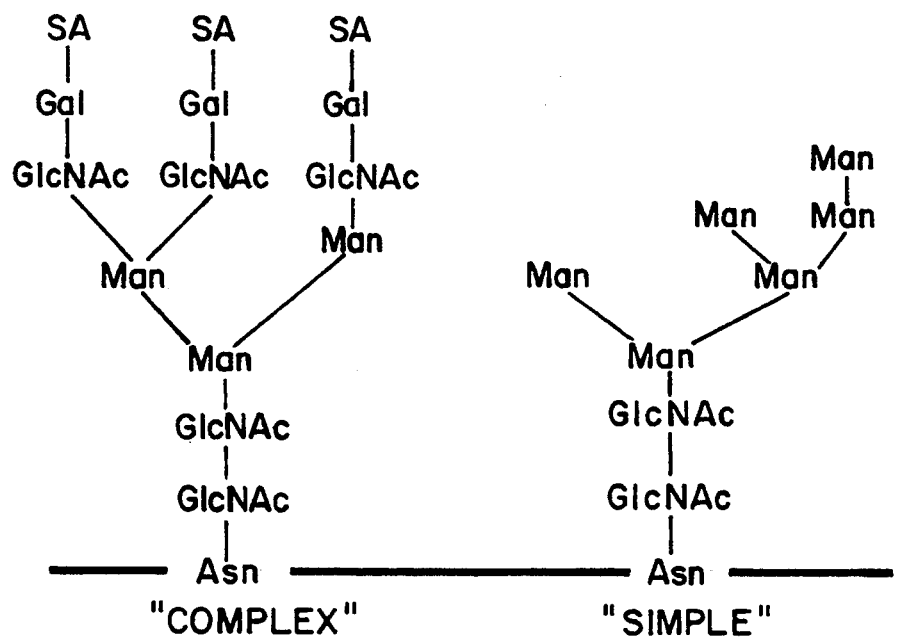
FIG. 1 depicts the N-linked glycosylation patterns of proteins produced from mammalian cells (a) and yeast (b), where SA is sialic acid, Gal is galactose, Man is mannose, GlcNAc is N-acetyl glucosamine, and Asn is asparagine.

As used herein, "plasminogen activator" refers to a protein that is capable of converting plasminogen to plasmin. Examples of such plasminogen activators include tissue-type plasminogen activator, urokinase, prourokinase, from any species, preferably human; streptokinase; and the like. These plasminogen activators may be produced, e.g., by recombinant cell culture systems, in bioactive forms. It will be understood that natural allelic variations exist and occur from individual to individual, demonstrated by (an) amino acid difference(s) in the overall sequence.

The expression "glycosylation sites at regions that are not glycosylated in the corresponding native plasminogen activator" refers to glycosylation sites, whether N— or O— linked, whether from yeast or mammalian hosts, and whether of complex, high mannose, or hybrid structure, that potentially or actually are glycosylated and are located in regions not actually or potentially glycosylated in the native molecule. Such actual or potential glycosylation sites in native t-PA and in native urokinase are indicated by circles in FIGS. 2 and 3, respectively. Thus, for example, while there are four potential sites for N-glycosidic linkage in the t-PA molecule (at Asn117, Asn184, Asn218, and Asn448), only three are actually glycosylated in the native t-PA (117,184 (in 50% of the molecules) and 448). While potentially a glycosylation site, the Asn218-Pro-Ser site in t-PA is not utilized for carbohydrate attachment in mammalian cells because of the presence of the proline in the sequence. See G. Pohl et al., *Biochemistry*, 23: 3701 (1984). In urokinase the glycosylation site occurs at position 302.

As used herein, "growth factor domain" refers to that region of the plasminogen activator that is structurally homologous with human and/or murine epidermal growth factors. See, e.g., Banyai et al., *FEBS Lett.*, 163: 37 (1983). In t-PA, this region is from amino acids about 44 to about 91; in prourokinase, this region is from about the N-terminal serine to about the 49th amino acid residue threonine; and in urokinase, this region is from about 5 to about 49. The DNA encoding a major portion of this domain in t-PA (residues 51 to 86) and partially encoding residues 50 and 87 is contained on a single exon, as reported by Ny et al., *Proc. Natl. Acad. Sci.* (U.S.A.), 81: 5355 (1984).

As used herein, "kringle 1 domain" refers to that region of t-PA that ranges from amino acids about 92 to about 173, and the "kringle domain" of urokinase refers to the region encompassing positions 50 to 136 of that molecule.

As used herein, the terms "human tissue plasminogen activator," "human t-PA," and "t-PA" denote human extrinsic (tissue-type) plasminogen activator having five functional regions consisting of a protease domain that is capable of converting plasminogen to plasmin, a kringle 1-containing domain, a kringle 2-containing domain believed to be responsible for fibrin binding, a finger domain and a growth factor domain. These three terms therefore include polypeptides containing these functional domains as part of the overall sequence.

A "two-chain cleavage site" in t-PA comprises at least the arginine residue at position 275. However, various amino acids adjacent to or within several residues of position 275 are also believed to be a part of the domain recognized by enzymes that convert plasminogen activator to its two-chain form. Thus, replacement of amino acids at positions other than 275 within the domain could result in mutant plasminogen activators that are resistant to conversion to the two-chain form.

In the particular embodiment, "single-chain plasminogen activator mutant" is a plasminogen activator that is resistant to conversion to the two-chain form. It is characterized by single or multiple amino acid substitutions at the two-chain activation site. As modified, such an activation site is not enzymatically recognized, and, therefore, not hydrolyzed by enzymes that normally convert plasminogen activator to its two-chain form. A noted example of such a mutant is a molecule resistant to cleavage at the 275/276 cleavage site by imposed modifications in the 275 to 279 region, for example, having an amino acid other than arginine such as glycine or glutamic acid at position 275 and glutamic acid at position 275 and isoleucine at position 277 (designated G275, E275, and E275,I277, respectively). These single-chain mutants are more fully described in copending U.S. Ser. No. 07/071,506, supra.

B. General Methods

1. Glycosylation

The plasminogen activator amino acid sequence variant must contain at least one amino acid sequence that has the potential to be glycosylated through an O— or N— linkage and that is not normally glycosylated in the native molecule.

If N-linked glycosylation is contemplated, the glycosylation site in the variant is a tripeptidyl sequence of the formula: asparagine-X-serine or asparagine-X-threonine, wherein asparagine is the acceptor and X is any of the twenty genetically encoded amino acids except proline, which prevents glycosylation. See D. K. Struck and W. J. Lennarz, in *The Biochemistry of Glycoproteins and Proteoglycans*, ed. W. J. Lennarz, Plenum Press, 1980, p. 35; R. D. Marshall, *Biochem. Soc. Symp.*, 40:17 (1974); and Winzler, R. J., in *Hormonal Proteins and Peptides* (ed. Li, C. I.) p. 1–15 (Academic Press, New York, 1973). The amino acid sequence variant herein is modified by either inserting the appropriate amino acid(s) at the proper site(s) to effect the glycosylation (as by adding the asparagine-X-serine(threonine) tripeptide after position 103 to make the surface loop larger and more exposed) or substituting for the amino acid(s) at the appropriate site(s) the appropriate amino acids to effect glycosylation.

If O—linked glycosylation is to be employed, O—glycosidic linkage occurs in animal cells between N—acetylgalactosamine, galactose, or xylose and one of several hydroxyamino acids, most commonly serine or threonine, but also in some cases a 5-hydroxyproline or 5-hydroxylysine residue placed in the appropriate region of the molecule.

Glycosylation patterns for proteins produced by mammals are described in detail in *The Plasma Proteins: Structure, Function and Genetic Control*, F. W. Putnam, ed., 2nd edition, volume 4 (Academic Press, New York, 1984), p. 271-315, the entire disclosure of which is incorporated herein by reference. In this chapter, asparagine-linked oligosaccharides are discussed, including their subdivision into at least three groups referred to as complex, high mannose, and hybrid structures, as well as O—glycosidically linked oligosaccharides.

Chemical and/or enzymatic coupling of glycosides to proteins can be accomplished using a variety of activated groups, for example, as described by Aplin and Wriston in *CRC Crit. Rev. Biochem.*, pp. 259-306 (1981), the disclosure of which is incorporated herein by reference. The advantages of the chemical coupling techniques are that they are relatively simple and do not need the complicated enzymatic machinery required for natural O— and N—linked glycosylation. Depending on the coupling mode used, the sugar(s) may be attached to (a) arginine or histidine, (b) free carboxyl groups such as those of glutamic acid or aspartic acid, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described more fully in PCT WO 87/05330 published Sep. 11, 1987, the disclosure of which is incorporated herein by reference.

Glycosylation patterns for proteins produced by yeast are described in detail by Tanner and Lehle, *Biochim. Biophys. Acta*, 906(1): 81-99 (1987) and by Kukuruzinska et al., *Annu. Rev. Biochem.*, 56: 915-944 (1987), the disclosures of which are incorporated herein by reference.

Figure 1B:
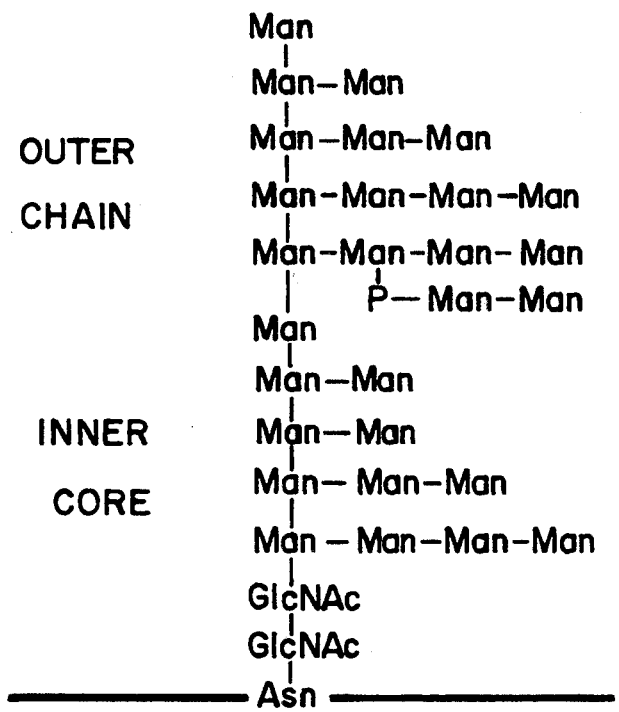

In addition, FIG. 1 depicts a comparison of the N—linked glycosylation patterns of proteins produced in mammalian cells versus yeast.

2. Amino Acid Sequence Variants

Figure 2:
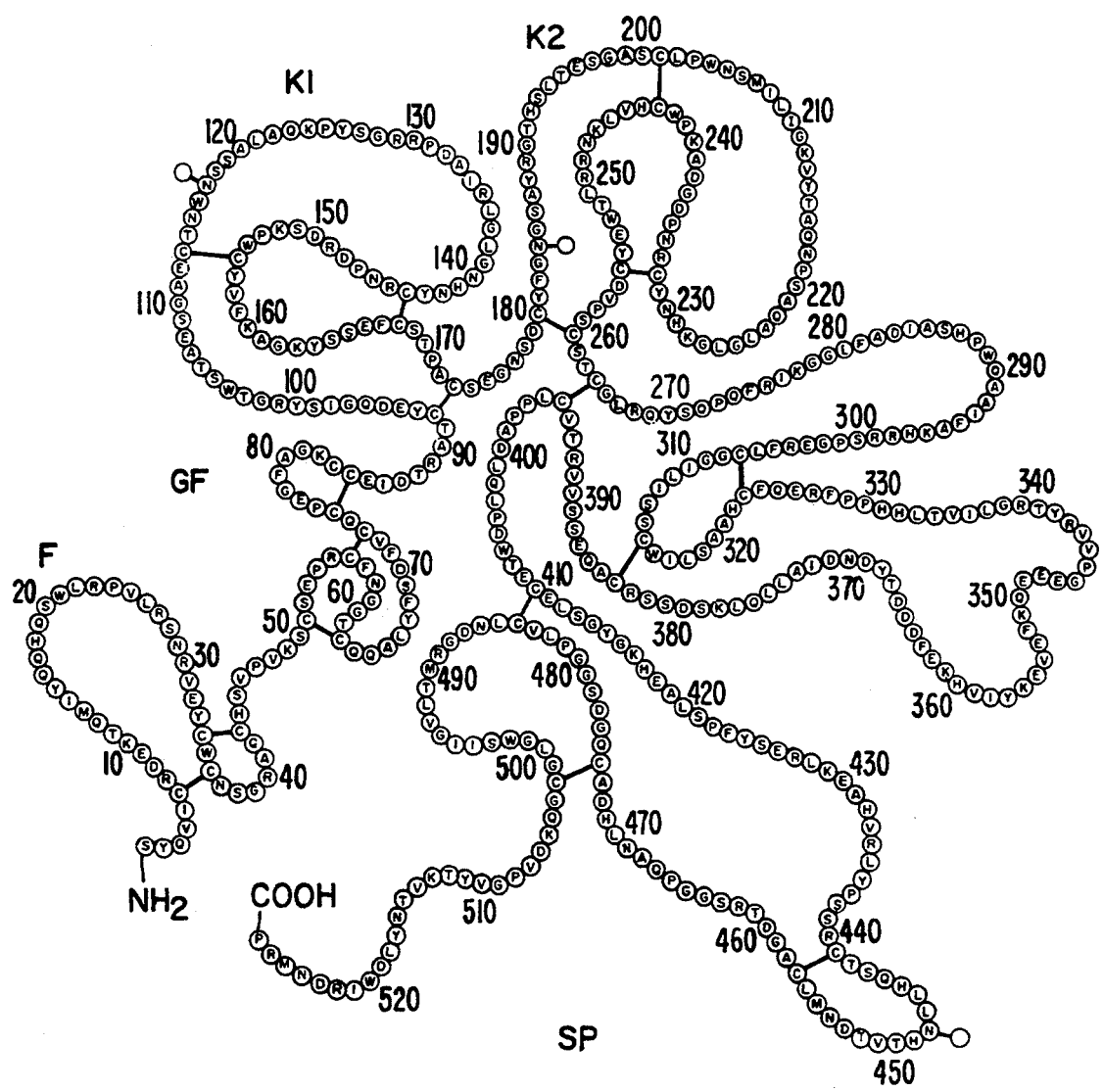
FIG. 2 depicts the primary structure of t-PA showing the location of the five domains, the disulfide bridging, and the glycosylation sites.
Figure 3:
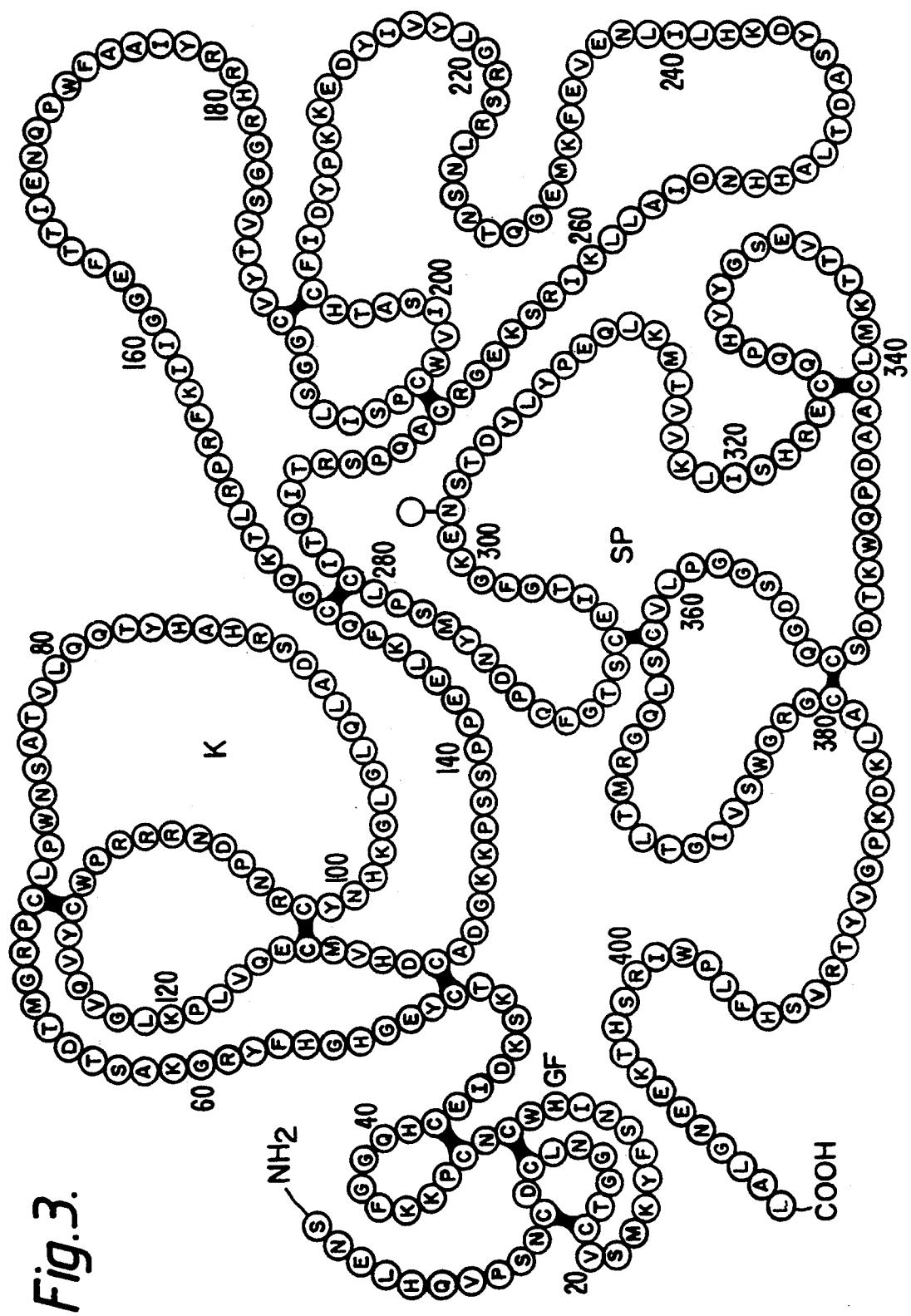
FIG. 3 depicts the primary structure of human urokinase showing the location of the three domains, the disulfide bridging, and the glycosylation site.

For purposes of discussing the variants herein, reference is made to FIGS. 2 and 3, which respectively illustrate the primary structures of t-PA and human urokinase.

In FIG. 2, the letters in the circles are single-letter amino acid codes, the connecting lines between chains indicate disulfide bridging, the open circles indicate glycosylation sites, and the designations F, GF, K1, K2, and SP indicate, respectively, the finger, growth factor, kringle 1, kringle 2, and serine protease domains.

In FIG. 3, the letters in the circles are single-letter amino acid codes, the connecting line between chains indicates disulfide bridging, the open circle indicates a glycosylation site, and the designations GF, K and SP indicate, respectively, the growth factor, kringle, and serine protease domains.

For purposes of shorthand designation of plasminogen activator variants described herein, it is noted that numbers refer to the amino acid residue/position along the amino acid sequences of putative mature t-PA (EPO Publ. No. 93,619), mature human urokinase, and prourokinase. Amino acid identification uses the single-letter alphabet of amino acids, i.e.,

| Asp | D | Aspartic acid | Ile | I | Isoleucine |
|-----|---|---------------|-----|---|------------|
| Thr | T | Threonine | Leu | L | Leucine |
| Ser | S | Serine | Tyr | Y | Tyrosine |
| Glu | E | Glutamic acid | Phe | F | Phenylalanine |
| Pro | P | Proline | His | H | Histidine |
| Gly | G | Glycine | Lys | K | Lysine |
| Ala | A | Alanine | Arg | R | Arginine |
| Cys | C | Cysteine | Trp | W | Tryptophan |
| Val | V | Valine | Gln | Q | Glutamine |
| Met | M | Methionine | Asn | N | Asparagine |

The number following such single letters refers to the amino acid position, e.g., D184 means a variant having, inter alia, an aspartic acid at position 184.

While the glycosylation site(s) for purposes of this invention may be any site(s) within the molecule that is not already or potentially glycosylated in the corresponding native protein, it is preferably in a position of the molecule that is exposed to the exterior. Such regions include, e.g., amino acid positions 57 to 63 to 69, and 78 to 82 (within the growth factor domain) of t-PA. These regions correspond to loops A, B, and C, respectively, of the type 1 growth factor domains shown in FIG. 2 of Appella et al., *FEBS Letters*, 231: 1-4 (1988), the disclosure of which is incorporated herein by reference. Thus, for O—linked glycosylation, one or more amino acids in these regions is replaced or supplemented with a serine, threonine, or 5-hydroxylysine residue.

Exemplary variants for N-linked glycosylation that employ these regions (where urokinase means human urokinase and also includes human prourokinase) include: S39 t-PA, N50 t-PA, S60 PA, S17 urokinase, T60 t-PA, T17 urokinase, N64S66 t-PA, N64T66 t-PA, S24 urokinase, T24 urokinase, N65S67 t-PA, N65T67 t-PA, N23S25 urokinase, N23T25 urokinase, N67 t-PA, N67T69 t-PA, N25 urokinase, N25T27 urokinase, N78S80 t-PA, N78T80 t-PA, N36S38 urokinase, N36T38 urokinase, N79S81 t-PA, N79T81 t-PA, N37S39 urokinase, N37T39 urokinase, N80S82 t-PA, N80T82 t-PA, N38S40 urokinase, N38T40 urokinase, N103 t-PA, or any combination of one loop with another, such as, e.g., S60N65T67 t-PA, N67N103 t-PA, or S60N78S80 t-PA.

In one preferred embodiment, the N-linked glycosylation site is the tyrosine-phenylalanine-serine tripeptidyl sequence at positions 67 to 69 of t-PA, and positions 25 to 27 of human urokinase and human prourokinase. In another preferred embodiment, the N—linked glycosylation site is the site at position 39 of t-PA, positions 50 to 52 of t-PA, position 60 of t-PA, and positions 103 to 105 of t-PA.

The plasminogen activator variants herein, in addition to being altered from the native sequence at one or more sites so as to effect potential or actual glycosylation at those sites where they are not ordinarily glycosylated, also optionally contain substitutions, deletions, or insertions of residues in other regions of the native sequence to improve certain properties of the molecule.

For example, the t-PA variants herein may be deglycosylated at known glycosylation sites, such as by removal of the glycosylation site(s) at positions 117, 184, 448, and 218.

As another example, the t-PA variants herein may be devoid of at least a portion of the finger domain, and/or devoid of glycosylation potential at the glycosylation site surrounding amino acid 184, and may exhibit resistance to proteolytic cleavage at the site surrounding amino acids 275 and 276 and/or having amino acid modifications in the putative lysine binding site of kringle 2.

In addition, fibrin binding of t-PA can be modulated, most preferably restored or increased, by appropriate substitutions of positively or negatively charged amino acid residues on the opposite edges of the putative ligand binding pocket of t-PA. The variants herein are generally prepared by site-directed mutagenesis or by excision/ligation techniques described further hereinafter.

Specific examples of such t-PA variants include a molecule devoid of amino acids 1 to 44 (designated des 1–44), a molecule having aspartic acid at position 184 (designated D184), and a single-chain plasminogen activator mutant. Variants devoid of amino acids 1 to 44 are described more fully in copending U.S. Ser. No. 68,448, supra, now abandoned.

All of the above t-PA variants are optionally modified in various other regions of the molecule, for example:

1. Kringle 1 modifications, for example, deletion of about 92 to 179, and/or
2. Kringle 2 modifications, for example, modification in the region of amino acids about 205–215, especially 210–213, and/or
3. Amino acids about 244–255, especially 252 or its site, and/or
4. Amino acids about 233–242, especially 236–238, and/or
5. Known glycosylation sites such as amino acid 184, and/or
6. Modifications that confer one or more of the following biological activities: zymogenic activity, fibrin specificity, or plasma clot specificity, consisting of an amino acid alteration (substitution, insertion, or deletion) in its protease domain as compared with the corresponding wild-type t-PA, which alteration is responsible for said biological activity.

These lattermost variants are described more fully in copending U.S. Ser. No. 07/384,608 filed Jul. 24, 1989, the disclosure of which is incorporated herein by reference. Preferably, the substitution is at position(s) 267, 283+287, 296–299, 303–304, 331–332, 339+342, 347–349+351, 364–366, 408, 410, 416–418, 426–427+4-29–430, 432+434, 440, 445+449, 449+453, 460+462, or 477 of the corresponding wild-type t-PA, where the "+" indicates alterations only at the positions designated, and the "-" indicates alterations at all positions designated.

Particular embodiments of the above-noted t-PA variants, with asparagine at position 67 or 103, are: des 1–44N67D184G275 t-PA, des 1–44N103D184G275 t-PA; des 1–44N67D184E275 t-PA, des 1–44N103D184E275 t-PA; des 1–44N67G275 t-PA, des 1–44N103G275 t-PA; des 1–44N67E275 t-PA, des 1–44N103E275 t-PA; des 1–44N67Q275I277 t-PA, des 1–44N103Q275I277 t-PA; des 1–44N67D184E275I277 t-PA, des 1–44N103D184E275I277 t-PA; des 1–44N67E275I277 t-PA, des 1–44N103E275I277 t-PA; des 1–44N67R210A211R212R213E275 t-PA, des 1–44N103R210A211R212R213E275 t-PA; des 1–44N67R210A211R212R213E275I277 t-PA, des 1–44N103R210A211R212R213E275I277 t-PA, des 1–44N67K213E275 t-PA, des 1–44N103K213E275 t-PA, des 1–44N67K213E275I277 t-PA, des 1–44N103K2-13E275I277 t-PA, des 1–44N67R252E275 t-PA, des 1–44N103R252E275 t-PA, des 1–44N67R252E275I277 t-PA, des 1–44N103R252E275I277 t-PA, des 1–44N67K210E275 t-PA, des 1–44N103K210E275 t-PA, des 1–44N67K210E275I277 t-PA, des 1–44N103K2-10E275I277 t-PA, des 1–44N67R210H211Q212K213E275 t-PA, des 1–44N103R210H211Q212K213E275 t-PA, des 1–44N67R210H211Q212K213E275I277 t-PA, des 1–44N103R210H211Q212K213E275I277 t-PA, des 1–44N67D184R210A211R212R213R252E275 t-PA, des 1–44N103D184R210A211R212R213R252E275 t-PA, des 1–44N67D184R210A211R212R213R252E275I277 t-PA, des 1–44N103D184R210A211R212R213R2-52E275I277 t-PA, N67-des 92–179D184R2-10A211R212R213R252E275 t-PA, N103-des 92–179D184R210A211R212R213R252E275 t-PA, N67A267 t-PA, N103A267 t-PA, N67A283A287 t-PA, N103A283A287 t-PA, N67A296A297AA298A299 t-PA, N103A296A297A298A299 t-PA, N67A303A304 t-PA, N103A303A304 t-PA, N67A331A332 t-PA, N103A331A332 t-PA, N67A339A342 t-PA, N103A33-9A342 t-PA, N67A347A348A349A351 t-PA, N103A347A348A349A351 t-PA, N67A364A365A366 t-PA, N103A364A365A366 t-PA, N67A408 t-PA, N103A408 t-PA, N67A410 t-PA, N103A410 t-PA, N67A416A417A418 t-PA, N103A416A417A418 t-PA, N67A426A427A429A430 t-PA, N103A426A427A42-9A430 t-PA, N67A432A434 t-PA, N103A432A434 t-PA, N67A440 t-PA, N103A440 t-PA, N67A445A449 t-PA, N103A445A449 t-PA, N67A449A453 t-PA, N103A449A453 t-PA, N67A460A462 t-PA, N103A46-0A462 t-PA, N67A477 t-PA, N103A477 t-PA, or the N184 and S184 analogues thereof, and combinations thereof.

Many of these modifications may significantly alter clearance rates and fibrin binding relative to native t-PA. The practitioner skilled in the art will be able to determine by the appropriate assay what the optimum properties of each variant are that are desired in any particular instance.

The modification to change or insert the appropriate amino acid(s) in the native molecule to effect the above sequence variations is accomplished by any means known in the art, such as, e.g., site-directed mutagenesis or ligation of the appropriate sequence into the DNA encoding the relevant protein, as described below.

3. Site-Specific Mutagenesis

Preparation of t-PA variants in accordance herewith is preferably achieved by site-specific mutagenesis of DNA that encodes an earlier prepared variant or a nonvariant version of the protein. Site-specific mutagenesis allows the production of t-PA variants through the use of specific oligonucleotide sequences that encode the DNA sequence of the desired mutation, as well as a sufficient number of adjacent nucleotides to provide a primer sequence of sufficient size and sequence complexity to form a stable duplex on both sides of the junction being traversed. Typically, a primer of about 20 to 25 nucleotides in length is preferred, with about 5 to 10 residues on both sides of the junction of the sequence being altered. In general, the technique of site-specific mutagenesis is well known in the art as exemplified by publications such as Adelman et al., *DNA*, 2: 183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981), the disclosure of which is incorporated herein by reference. These phage are readily commercially available and their use is generally well known to those skilled in the art. Alternatively, plasmid vectors that contain a single-stranded phage origin of replication (Veira et al., *Meth. Enzymol.*, 153:3 (1987)) may be employed to obtain single-stranded DNA.

In general, site-directed mutagenesis in accordance herewith is performed by first obtaining a single-stranded vector that includes within its sequence a DNA sequence that encodes the relevant plasminogen activator. An oligonucleotide primer bearing the desired mutated sequence is prepared, generally synthetically, for example, by the method of Crea et al., *Proc. Natl. Acad. Sci.* (USA), 75: 5765 (1978). This primer is then annealed with the single-stranded t-PA sequence-containing vector, and subjected to DNA-polymerizing enzymes such as *E. coli* polymerase I Klenow fragment, to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as JM101 cells and clones are selected that include recombinant vectors bearing the mutated sequence arrangement.

After such a clone is selected, the mutated t-PA region is removed and placed in an appropriate vector for t-PA production, generally an expression vector of the type that typically is employed for transformation of an appropriate eukaryotic host. In the context of the present invention, CHO cells or 293 (human kidney cells described by Graham et al., *J. Gen. Virol.*, 36: 59 (1977)) are preferred for the preparation of long-term stable t-PA producers. However, the invention is not limited to CHO production as it is known that numerous other cell types may be employed, particularly where one desires only transient production of the enzyme for test purposes. For example, described below is a transient system employing 293 cells that provides a convenient system for production of t-PA variants for analytical purposes.

4. Cleavage/Ligation Technique

Another method for making mutations in the DNA sequence encoding the plasminogen activator so as to introduce a new glycosylation site involves cleaving the DNA encoding the plasminogen activator at the appropriate position by digestion with restriction enzymes, recovering the properly cleaved DNA, synthesizing an oligonucleotide encoding the desired amino acid sequence for glycosylation and flanking regions such as polylinkers with blunt ends (or, instead of using polylinkers, digesting the synthetic oligonucleotide with the restriction enzymes also used to cleave the activator-encoding DNA, thereby creating cohesive termini), and ligating the synthetic DNA into the remainder of the plasminogen-activator-encoding structural gene.

5. Host Cell Cultures and Vectors

Although Chinese hamster ovary (CHO) expression is ultimately preferred for t-PA production, the vectors and methods disclosed herein are suitable for use in host cells over a wide range of eukaryotic organisms that effect glycosylation of proteins.

In general, of course, prokaryotes are preferred for the initial cloning of DNA sequences and constructing the vectors useful in the invention. For example, *E. coli* K12 strain 294 (ATCC No. 31,446) is particularly useful. Other microbial strains that may be used include *E. coli* strains such as *E. coli* B, and *E. coli* X1776 (ATCC No. 31,537). These examples are, of course, intended to be illustrative rather than limiting.

For expression, eukaryotic hosts, such as yeast and mammalian cultures, are used. *Saccharomyces cerevisiae*, or common baker's yeast, is the most commonly used among eukaryotic microorganisms, although a number of other strains are commonly available. For expression in Saccharomyces, the plasmid YRp7, for example (Stinchcomb et al., *Nature*, 282:39 (1979); Kingsman et al., *Gene*, 7: 141 (1979); Tschemper et al., *Gene*, 10:157 (1980)) is commonly used. This plasmid already contains the trpl gene that provides a selection marker for a mutant strain of yeast lacking the ability to grow in tryptophan, for example, ATCC No. 44,076 or PEP4-1 (Jones, *Genetics*, 85: 12 (1977)). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., *J. Biol. Chem.*, 255:2073 (1980)) or other glycolytic enzymes (Hess et al., *J. Adv. Enzyme Reg.*, 7: 149 (1968); Holland et al., *Biochemistry*, 17: 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions, are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

In addition to eukaryotic microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years [*Tissue Culture*, Academic Press, Kruse and Patterson, editors (1973)]. Examples of such useful host cell lines are VERO and HeLa cells, Chinese hamster ovary (CHO) cell lines, and W138, BHK, COS-7, 293, and MDCK cell lines. Expression vectors for such cells ordinarily include (if necessary) an origin of replication, a promoter located in front of the gene to be expressed, along with any necessary ribosome binding sites, RNA splice sites, polyadenylation sites, and transcriptional terminator sequences.

For use in mammalian cells, the control functions on the expression vectors are often provided by vital material. For example, commonly used promoters are derived from polyoma, Adenovirus2, and most frequently Simian Virus 40 (SV40). The early and late promoters of SV40 virus are particularly useful because both are obtained easily from the virus as a fragment that also contains the SV40 viral origin of replication (Fiers et al., Nature, 273:113 (1978)). Smaller or larger SV40 fragments may also be used, provided there is included the approximately 250-bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

In selecting a preferred host cell for transfection by the vectors of the invention that comprise DNA sequences encoding both variant t-PA and DHFR protein, it is appropriate to select the host according to the type of DHFR protein employed. If wild-type DHFR protein is employed, it is preferable to select a host cell that is deficient in DHFR, thus permitting the use of the DHFR coding sequence as a marker for successful transfection in selective medium that lacks hypoxanthine, glycine, and thymidine. An appropriate host cell in this case is the CHO cell line deficient in DHFR activity, prepared and propagated as described by Urlaub and Chasin, Proc. Natl. Acad. Sci. (USA) 77: 4216 (1980).

On the other hand, if DHFR protein with low binding affinity for MTX is used as the controlling sequence, it is not necessary to use DHFR-deficient cells. Because the mutant DHFR is resistant to methotrexate, MTX-containing media can be used as a means of selection provided that the host cells are themselves methotrexate sensitive. Most eukaryotic cells that are capable of absorbing MTX appear to be methotrexate sensitive. One such useful cell line is a CHO line, CHO-K1 (ATCC No. CCL 61).

Satisfactory amounts of human t-PA are produced by cell cultures; however, refinements, using a secondary coding sequence, serve to enhance production levels even further. The secondary coding sequence comprises dihydrofolate reductase (DHFR) that is affected by an externally controlled parameter, such as methotrexate, thus permitting control of expression by control of the methotrexate (MTX) concentration.

In terms of choosing the best host for the glycosylation, the selection will depend on the type of glycosylation desired, as, for example, yeast hosts will glycosylate differently from mammalian hosts, in terms of the number and types of sugars attached to the protein being expressed.

6. Typical Cloning and Expression Methodology Employable

If cells without formidable cell membrane barriers are used as host cells, transfection is carried out by the calcium phosphate precipitation method as described by Graham and Van der Eb, Virology, 52: 546 (1978). However, other methods for introducing DNA into cells such as by nuclear injection or by protoplast fusion may also be used.

If prokaryotic cells or cells that contain substantial cell wall constructions are used, the preferred method of transfection is calcium treatment using calcium as described by Cohen et al., Proc. Natl. Acad. Sci. (USA) 69:2110 (1972).

Construction of suitable vectors containing the desired coding and control sequences employ standard ligation techniques. Isolated plasmids or DNA fragments are cleaved, tailored, and religated in the form desired to construct the plasmids required.

Cleavage is performed by treating with restriction enzyme (or enzymes) in suitable buffer. In general, about 1 μg plasmid or DNA fragments is used with about 1 unit of enzyme in about 20 μl of buffer solution. (Appropriate buffers and substrate amounts for particular restriction enzymes are specified by the manufacturer.) Incubation times of about one hour at 37° C. are workable. After incubation, protein is removed by extraction with phenol and chloroform, and the nucleic acid is recovered from the aqueous fraction by precipitation with ethanol.

If blunt ends are required, the preparation may be treated for 15 minutes at 15° C. with 10 units of Polymerase I (Klenow), phenol chloroform extracted, and ethanol precipitated.

Size separation of the cleaved fragments is performed using 6 percent polyacrylamide gel described by Goeddel et al., Nucleic Acids Res., 8: 4057 (1980).

For ligation approximately equimolar amounts of the desired components, suitably end tailored to provide correct matching, are treated with about 10 units T4 DNA ligase per 0.5 μg DNA. (When cleaved vectors are used as components, it may be useful to prevent religation of the cleaved vector by pretreatment with bacterial alkaline phosphatase.)

As discussed above, t-PA variants are preferably produced by means of specific mutation. Mutants useful in the practice of the present invention are formed most readily through the use of specific oligonucleotide sequences that encode the DNA sequence of the desired mutation, as well as a sufficient number of adjacent nucleotides, to provide a sequence of sufficient size and sequence complexity to form a stable duplex on both sides of the mutation site being traversed.

For analysis to confirm correct sequences in plasmids constructed, the ligation mixtures are typically used to transform E. coli K12 strain 294 (ATCC 31,446) or other suitable E. Coli strains, and successful transformants selected by ampicillin or tetracycline resistance where appropriate. Plasmids from the transformants are prepared and analyzed by restriction mapping and/or DNA sequencing by the method of Messing et al., Nucleic Acids Res., 9: 309 (1981) or by the method of Maxam et al., Methods of Enzymology, 65: 499 (1980).

After introduction of the DNA into the mammalian cell host and selection in medium for stable transfectants, amplification of DHFR-protein-coding sequences is effected by growing host cell cultures in the presence of approximately 200–500 nM concentrations of methotrexate, a competitive inhibitor of DHFR activity. The effective range of concentration is highly dependent, of course, upon the nature of the DHFR gene, protein and the characteristics of the host. Clearly, generally defined upper and lower limits cannot be ascertained. Suitable concentrations of other folic acid analogs or other compounds that inhibit DHFR could also be used. MTX itself is however, convenient, readily available, and effective.

In order to simplify the examples certain frequently occurring methods will be referenced by shorthand phrases.

"Plasmids" are designated by a lower case p followed by an alphanumeric designation. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Digestion" of DNA refers to catalytic cleavage of the DNA with an enzyme that acts only at certain locations in the DNA. Such enzymes are called restriction enzymes, and the site for which each is specific is called a restriction site. The various restriction enzymes used herein are commercially available and their reaction conditions, cofactors and other requirements as established by the enzyme suppliers were used. Restriction enzymes commonly are designated by abbreviations composed of a capital letter followed by other letters representing the microorganism from which each restriction enzyme originally was obtained and then a number designating the particular enzyme. In general, about 1 $\mu$g of plasmid or DNA fragment is used with about 2 units of enzyme in about 20 $\mu$l of buffer solution. Appropriate buffers and substrate amounts for particular restriction enzymes are specified by the manufacturer. Incubation times of about 1 hour at 37° C. are ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (T. Maniatis et al., *Molecular Cloning: A Laboratory Manual,* (Cold Spring Harbor Laboratory; New York, 1982), pp. 133–134).

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see R. Lawn et al., 1981, *Nucleic Acids Res,* 9:6103–6114, and D. Goeddel et al., 1980, *Nucleic Acids Res,* 8: 4057.

"Southern Analysis" is a method by which the presence of DNA sequences in a digest or DNA-containing composition is confirmed by hybridization to a known, labelled oligonucleotide or DNA fragment. For the purposes herein, unless otherwise provided, Southern analysis shall mean separation of digests on 1 percent agarose, denaturation and transfer to nitrocellulose by the method of E. Southern, 1975, *J. Mol. Biol.* 98: 503–517, and hybridization as described by T. Maniatis et al., 1978, *Cell* 15: 687–701.

"Transformation" means introducing DNA into an organism so that the DNA is replicable, either as an extrachromosomal element or chromosomal integrant. Unless otherwise provided, the method used herein for transformation of *E. coli* is the CaCl$_2$ method of Mandel et al., 1970, *J. Mol. Biol.* 53: 154.

"Ligation" refers to the process of forming phosphodiester bonds between two double-stranded nucleic acid fragments (T. Maniatis et al., supra., p. 146). Unless otherwise provided, ligation may be accomplished using known buffers and conditions with 10 units of T4 DNA ligase ("ligase") per 0.5 $\mu$g of approximately equimolar amounts of the DNA fragments to be ligated.

"Preparation" of DNA from transformants means isolating plasmid DNA from microbial culture. Unless otherwise provided, the alkaline/SDS method of Maniatis et al., supra., p. 90, may be used.

"Oligonucleotides" are short-length single- or double-stranded polydeoxynucleotides that are chemically synthesized by known methods and then purified on polyacrylamide gels.

C. Purification

The t-PA variant preferably is recovered from the culture medium as a secreted protein, although it also may be recovered from host cell lysates when directly expressed without a secretory signal. When the variant is expressed in a recombinant cell other than one of human origin, the variant is thus completely free of proteins of human origin. However, it is necessary to purify the variant from recombinant cell proteins in order to obtain preparations that are substantially homogeneous as to protein. As a first step, the culture medium or lysate is centrifuged to remove particulate cell debris.

The variant is then purified from contaminant soluble proteins, for example, by fractionation on immunoaffinity or ion exchange columns; ethanol precipitation; reverse phase HPLC; chromatography on silica or on a cation-exchange resin such as DEAE; chromatofocusing; SDS-PAGE; ammonium sulfate precipitation; or gel electrophoresis using, for example, Sephadex G-75. A protease inhibitor that does not interfere with the t-PA activity such as phenylmethylsulfonyl fluoride PMSF also may be useful to inhibit proteolytic degradation during purification, and antibiotics may be included to prevent the growth of adventitious contaminants. One skilled in the art will appreciate that purification methods suitable for native t-PA may require modification to account for changes in the character of t-PA or its variants upon expression in recombinant cell culture.

In a preferred embodiment, the t-PA variant is secreted, and the supernatant is passed over a PBS-preconditioned column of glass beads coupled to anti-t-PA goat polyclonal A6 antibody, the column is equilibrated with a buffer, and the t-PA variant is then eluted.

D. Pharmaceutical Compositions

The compounds of the present invention can be formulated according to known methods to prepare pharmaceutically useful compositions, whereby the plasminogen activator product hereof is combined in admixture with a pharmaceutically acceptable carrier vehicle. Suitable carrier vehicles and their formulation, inclusive of other human proteins, e.g., human serum albumin, are described, for example, in *Remington's Pharmaceutical Sciences,* 16th ed., 1980, Mack Publishing Co., edited by Oslo et al., the disclosure of which is hereby incorporated by reference. Such compositions will typically contain an effective amount of the variant herein, for example, from about 0.5 to about 5 mg/ml, together with a suitable amount of carrier vehicle to prepare pharmaceutically acceptable compositions suitable for effective administration to the host. The plasminogen activator variant herein may be administered parenterally to subjects suffering from cardiovascular diseases or conditions, or by other methods that ensure its delivery to the bloodstream in an effective form.

Compositions particularly well suited for the clinical administration of variant plasminogen activator products employed in the practice of the present invention include, for example, sterile aqueous solutions, or sterile hydratable powders such as lyophilized protein. It is generally desirable to include further in the formulation an appropriate amount of a pharmaceutically acceptable salt, generally in an amount sufficient to render the formulation isotonic. A pH regulator such as arginine base, and phosphoric acid, are also typically included in sufficient quantities to maintain an appropriate pH, generally from 5.5 to 7.5. Moreover, for improvement of shelf-life or stability of aqueous formulations, it may also be desirable to include further agents such as glycerol. In this manner, variant t-PA formulations are rendered appropriate for parenteral administration, and, in particular, intravenous administration.

Dosages and desired drug concentrations of pharmaceutical compositions of the present invention may vary depending on the particular use envisioned. For example, in the treatment of deep vein thrombosis or peripheral vascular disease, "bolus" doses, on the order of about 0.05 to about 0.3 mg/kg, will typically be preferred with subsequent administrations, on the order of about 0.1 to about 0.2 mg/kg, being given to maintain an approximately constant blood level, preferably on the order of about 3 μg/ml.

However, for use in connection with emergency medical care facilities where infusion capability is generally not available and due to the generally critical nature of the underlying disease (e.g., embolism, infarct), it will generally be desirable to provide somewhat larger initial doses, such as an intravenous bolus on the order of about 0.3 mg/kg.

For example, the plasminogen activator variant hereof may be administered parenterally to subjects suffering from cardiovascular diseases or conditions. Dosage and dose rate may be parallel to that currently in use in clinical investigations of other cardiovascular, thrombolytic agents, e.g., about 1-2 mg/kg body weight as an intravenous or intra-arterial dose over 1.5 to 12 hours in human patients suffering from myocardial infarction, pulmonary embolism, etc.

As one example of an appropriate dosage form, a vial containing 50 mg t-PA, arginine, phosphoric acid, and polysorbate 80 may be reconstituted with 50 ml sterile water for injection and mixed with a suitable volume of 0.9 percent sodium chloride injection.

The slower clearance rates of plasminogen activator variants herein may be suitable for rapid intravenous injection, particularly as a bolus, for example. This would eliminate the need for complex administration procedures and may increase the opportunity for the use of the plasminogen activator in settings with limited medical equipment such as in emergency vehicles staffed with paramedic personnel. A slower clearance rate of plasminogen activator variants herein may also allow lower, safer initial doses and could maintain thrombolytically effective plasma levels for up to 45 minutes or longer. The variants herein with slower clearance rate may also be useful for low-dose extended therapy that may be necessary to avoid reocclusion following successful acute thrombolysis or for extended thrombolysis that may be necessary in cases of peripheral vascular occlusion.

The following examples are intended merely to illustrate the best mode now known for practicing the invention, but the invention is not to be considered limited thereto.

All literature citations herein are expressly incorporated by reference.

EXAMPLE I

A. Preparation and Utilization of Expression Vectors for Recombinant Production Of the t-PA Variants Hereof 1. Construction of Plasmid p7-1H a) Plasmid pCISt-PA Plasmid pCISt-PA was prepared as described, for example, in U.S. Ser. No. 07/071,506, filed July 9, 1987, Supra. In recapitulation, the vector pCIHt-PA containing the cytomegalovirus enhancer and promoter, the cytomegalovirus splice donor site and intron, the Ig variable region splice acceptor site, the cDNA-encoding t-PA (Pennica et al., Nature,. 301: 214 (1983)) and the hepatitis surface antigen polyadenylation and transcription termination site was constructed first:

The vector pF8CIS containing the cytomegalovirus enhancer (Boshart et al., Cell, 41: 520 (1985)) and promoter (Thomsen et al., Proc. Natl. Acad. Sci. (U.S.A.) 81: 659 (1984)), the cytomegalovirus splice donor site and a portion of an intron (Sternberg et al., J. of Virol., 49: 190 (1984)), the Ig variable region intron and splice acceptor site, the cDNA encoding factor VIII, and the SV40 polyadenylation site was constructed. The three parts of the construction are detailed below.

1. The ampicillin resistance marker and replication origin of the final vector was derived from the starting plasmid pUC13pML, a variant of the plasmid pML (Lusky et al., Nature, 293: 79 (1981)). pUC13pML was constructed by transferring the polylinker of pUC13 (Veira et al., Gene, 19: 259 (1982)) to the EcoRI and HindIII sites of pML. A second starting plasmid pUC8CMV was the source of the CMV enhancer, promoter and splice donor sequence. pUC8CMV was constructed by inserting nucleotides 1 through 732 for the CMV enhancer, promoter and splice donor sequence into the blunted PstI and SphI sites of pUC8—Veira et al., supra. Synthetic BamHI-HindIII linkers (commercially available from New England Biolabs) were ligated to the cohesive BamHI end, creating a HindIII site. Following this ligation a HindIII-HincII digest was performed. This digest yielded a fragment of approximately 800 bp that contained the CMV enhancer, promoter and splice donor site. Following gel isolation, this 800-bp fragment was ligated to a 2900-bp piece of pUC13pML. The fragment required for the construction of pF8CIS was obtained by digestion of the above intermediate plasmid with SalI and HindIII. This 3123-bp piece contained the resistance marker for ampicillin, the origin of replication from pUC13pML, and the control sequences for the CMV, including the enhancer, promoter, and splice donor site.

2. The Ig variable region intron and splice acceptor sequence was constructed using a synthetic oligomer. A 99-mer and a 30-mer were chemically synthesized having the following sequence for the IgG intron and splice acceptor site (Bothwell et al., Cell, 24: 625 (1981)):

```
  1  5'-AGTAGCAAGCTTGACGTGTGGCAGGCTTGA...
 31     GATCTGGCCATACACTTGAGTGACAATGA...
 60     CATCCACTTTGCCTTTCTCTCCACAGGT...
 88     GTCCACTCCCAG-3'
  1  3'-CAGGTGAGGGTGCAGCTTGACGTCGTCGGA-5'
```

DNA polymerase I (Klenow fragment) filled in the synthetic piece and created a double-stranded fragment (Wartell et al., Gene, 9: 307 (1980)). This was followed by a double digest of PstI and HindIII. This synthetic linker was cloned into pUC13 (Veira et al., supra) at the PstI and HindIII sites. The clone containing the synthetic oligonucleotide, labeled pUCIg.10, was digested with PstI. A ClaI site was added to this fragment by use of a PstI-ClaI linker. Following digestion with HindIII a 118-bp piece containing part of the Ig intron and the Ig variable region splice acceptor was gel isolated.

3. The third part of the construction scheme replaced the hepatitis surface antigen 3' end with the polyadenylation site and transcription termination site of the early region of SV40. A vector, pUC.SV40, containing the SV40 sequences was inserted into pUC8 at the BamHI site described in Veira et al., supra. pUC.SV40 was then digested with EcoRI and HpaI. A 143-bp fragment containing only the SV40 polyadenylation site was gel isolated from this digest. Two additional fragments were gel isolated following digestion of pSVE.8c1D (EPO Pub. No. 160,457). The 4.8-kb fragment generated by EcoRI and ClaI digest contains the SV40-DHFR transcription unit, the origin of replication of pML, and the ampicillin resistance marker. The 7.5-kb fragment produced following digestion with ClaI and HpaI contains the cDNA for Factor VIII. A three-part ligation yields pSVE.8c24D. This intermediate plasmid was digested by ClaI and SalI to give a 9611-bp fragment containing the cDNA for Factor VIII with the SV40 polyadenylation and transcription termination sites followed by the SV40 DHFR transcription unit.

The final three-part ligation to yield pF8CIS used: a) the 3123-bp SalI-HindIII fragment containing the origin of replication, the ampicillin resistance marker and the CMV enhancer, promoter and splice donor; b) the 118-bp HindIII-ClaI fragment containing the Ig intron and splice acceptor; and c) a 9611-bp ClaI-SalI fragment containing the cDNA for Factor VIII, SV40 polyadenylation site, and the SV40 DHFR transcription unit.

Figure 4A:
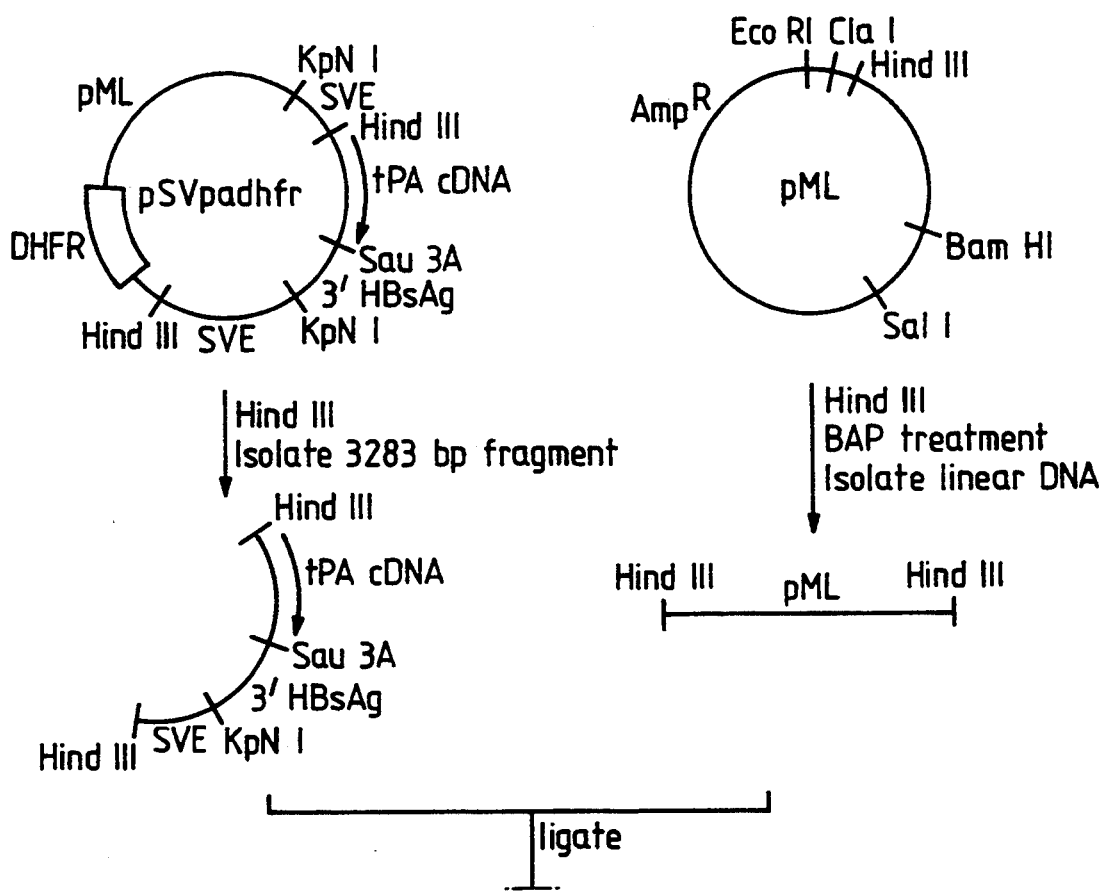
Figure 4B:
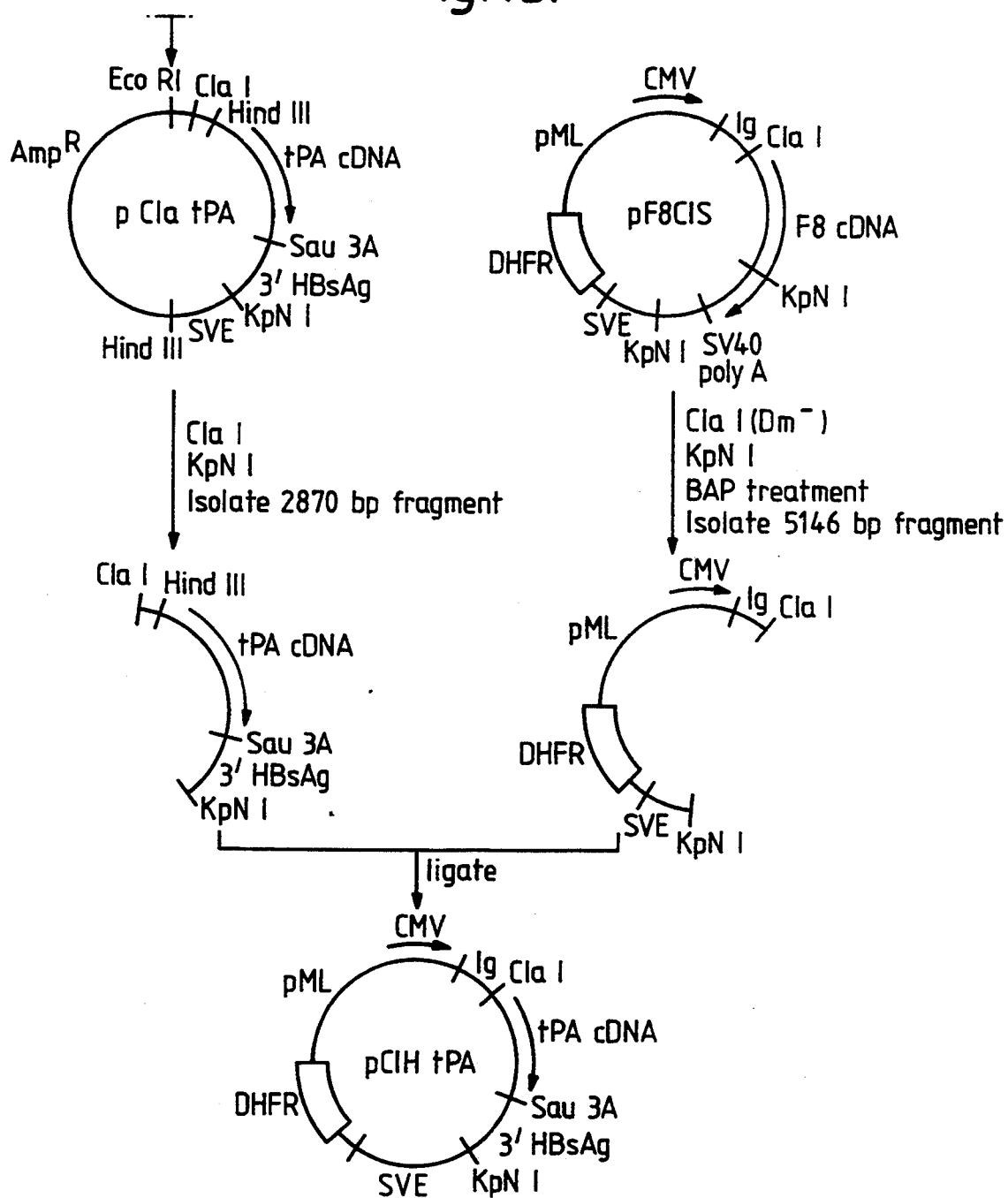

Next, the completion of the construction of plasmid pCIHt-PA from intermediate plasmid pCla t-PA and plasmid pF8CIS (above) was undertaken:

The t-PA cDNA was first cloned into pML to provide a ClaI site at the 5' end of the gene. To do this, a 3238-bp HindIII fragment from pSVpa-DHFR (otherwise referred to as pETPFR, supra) was inserted into the HindIII site of pML (Lusky et al., supra). Colonies were screened for clones that have the 5' end of the cDNA juxtaposed to the ClaI site. The intermediate plasmid was labeled pCLAt-PA. A -tPA cDNA followed by the 3'- polyadenylation regions was isolated as a ClaI-KpnI fragment of 2870 bp. This fragment was ligated to the 5146-bp fragment of pF8CIS. This ClaI-KpnI fragment of the CIS vector provided the 5' control region, a SV40-DHFR transcriptional unit, the ampicillin resistance gene, and the origin region from pML. See FIG. 4.

Expression levels of t-PA were obtained by transfecting CHO or 293 cells with pCIHt-PA, in accordance with methods generally known per se and described supra. Media from the transfected 293 cells, for example, were assayed, demonstrating that pCIHt-PA produced 420 ng/ml of t-PA.

Figure 5A:
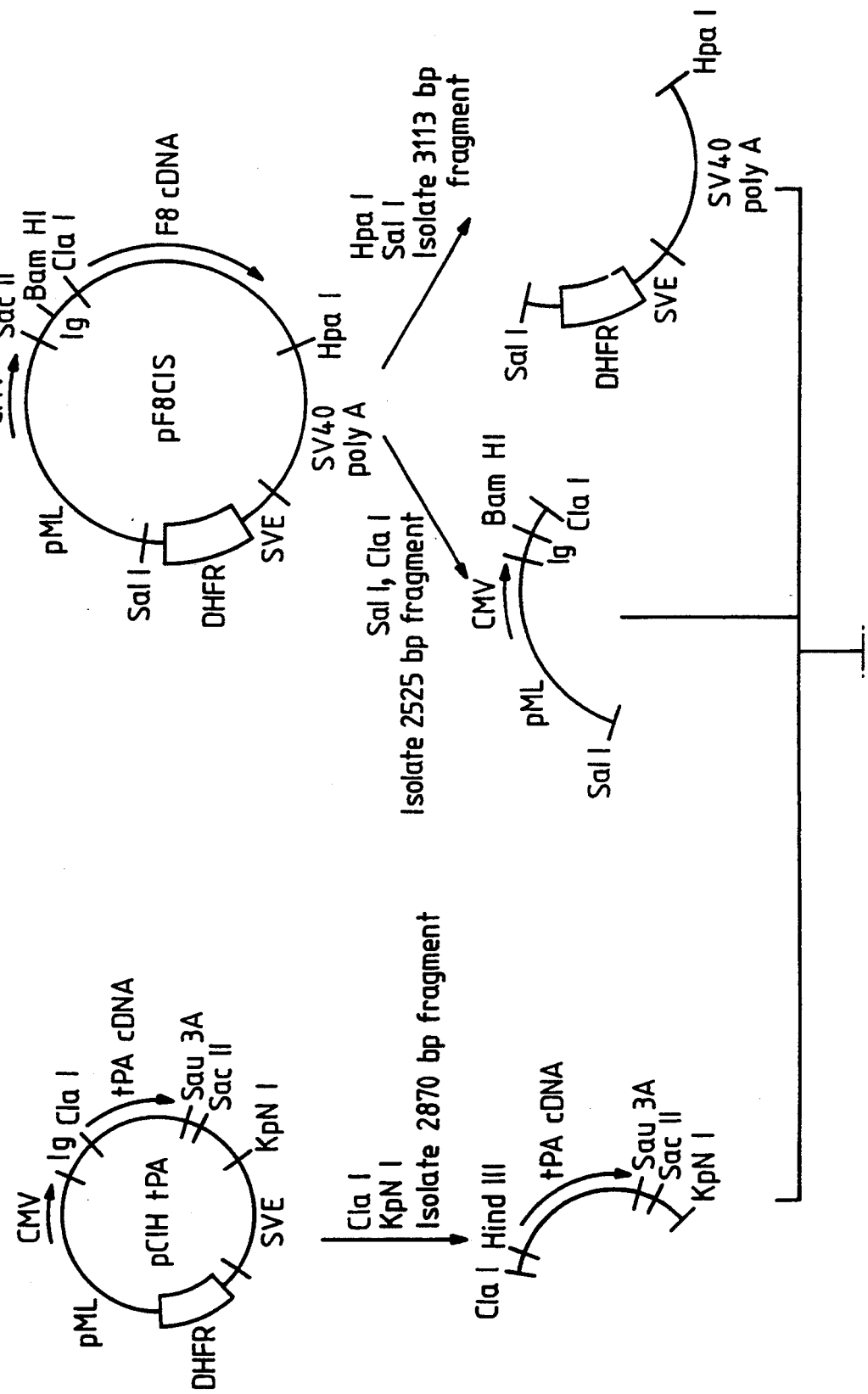

The vector pCISt-PA containing the cytomegalovirus enhancer and promoter, the cytomegalovirus splice donor site and intron, the Ig variable region splice acceptor site, the cDNA encoding t-PA, and the pSV40 polyadenylation sequence was finally constructed as follows:

The starting vectors for this construction were pCIHt-PA and. pF8CIS (Supra). The latter vector has the same 5' controls as pCIHt-PA, but includes the cDNA for Factor VIII and the SV40 polyadenylation site. SacII was used to cleave 3' of the t-PA cDNA. The resultant 3' overhang was blunted by T4 polymerase. pCIHt-PA was then cut with ClaI. This site separates the chimeric intron cleaving between the CMV intronic sequences and the Ig variable region intron. An 2870-bp fragment was gel isolated from the ClaI treatment. The SV40 polyadenylation site, DHFR, transcription control, bacterial origin of replication, and $amp^r$ gene, as well as the CMV enhancer and promoter and splice donor were isolated from pF8CIS. These elements were isolated into fragments as a 2525-bp Sal-BamHI fragment and a HpaI-Sal and 3113-bp fragment. A three-part ligation of the KpnI (blunt)-ClaI fragment with the HpaI-Sal fragment and Sal to BamHI fragment yields pCISt-PA, which was expressed in both CHO and 293 cells as discussed above for plasmid pCIHt-PA, giving 55 and 3000 ng/ml of t-PA, respectively. See FIG. 5.

b) Final Construction of p7-1H

Figure 6:
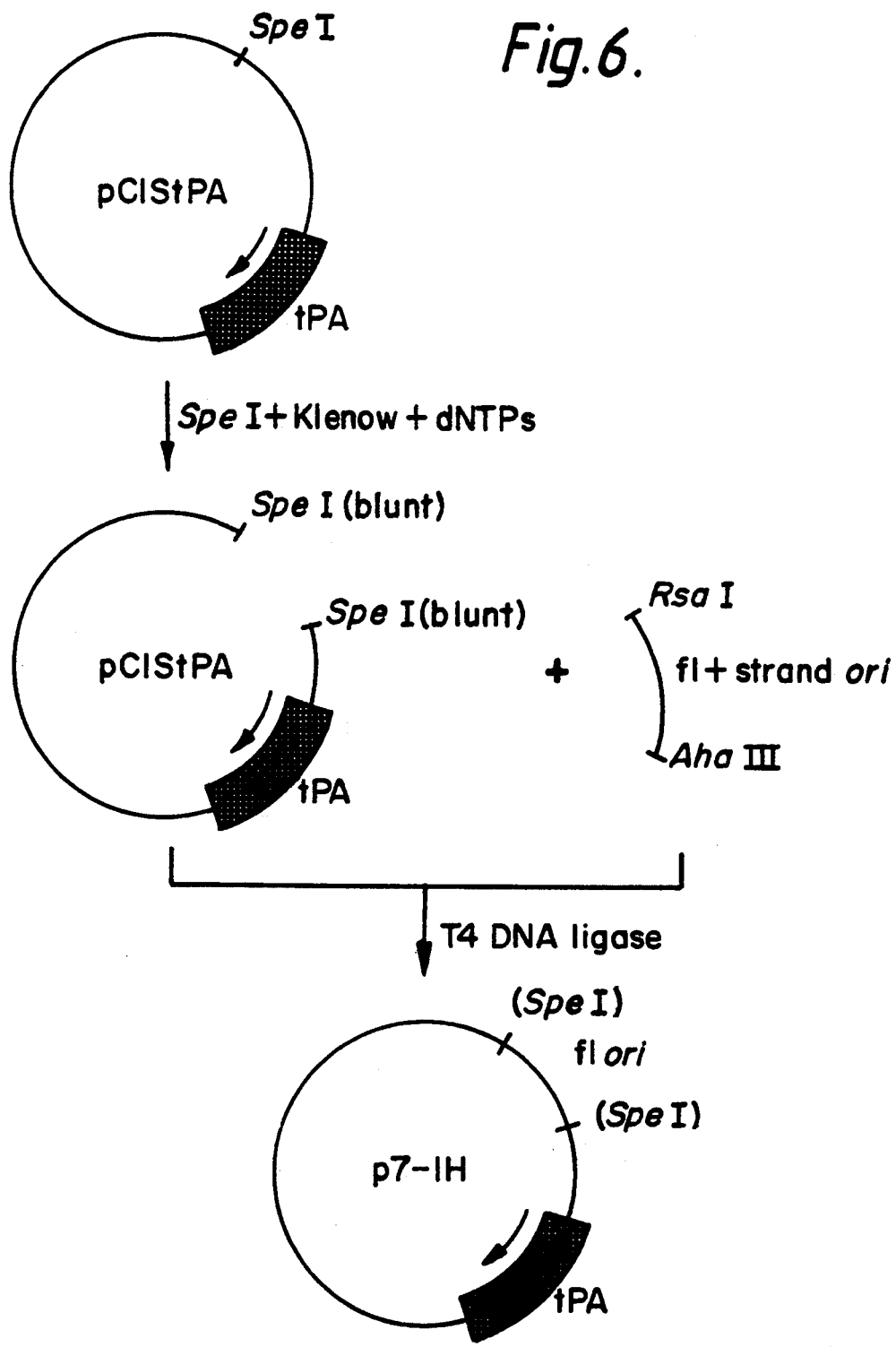
FIG. 6 is a schematic representation of a suitable method for the preparation of p7-1H, together with a description of certain of its prominent restriction sites.

The plasmid pCISt-PA was digested with SpeI, then treated with E. coli DNA polymerase I large fragment (Klenow) and deoxyribonucleoside triphosphates to create blunt ends. The resulting linear fragment was ligated, using T4 DNA ligase, to the 0.45kb-RsaI/AhaIII fragment containing the + strand origin from the single-stranded DNA phage, f1, as described in Zinder et al., Microbiol, REV., 49: 101 (1985). Ligation products were isolated with the f1 origin inserted in both possible orientations at the SpeI site of the pCISt-PA fragment. A plasmid containing this origin, in such an orientation that the anti-sense strand of the t-PA gene was packaged into virions in the presence of helper phage, was chosen and termed p7-1H. See FIG. 6.

2. Mutagenesis Examples a) Template Preparation

Plasmid p7-1H was introduced into E. coli strain JM101 (ATCC No. 33,876) via $CaCl_2$-mediated transformation. These cells were then infected with the helper virus M13K07 and single-stranded p7-1H DNA was prepared as described by Veira et al., Meth. Enzymol., 153: 3 (1987). Briefly, to 0.3 ml of a saturated culture of transformed cells in 2YT broth was added $10^9$–$10^{10}$ pfu of M13K07 and the mixture was incubated for 15 min. at 37° C. 1.5 ml of fresh 2YT broth, containing 50 µg/ml carbenicillin, was added and the culture was gently shaken for 16 hours at 37° C. After the cells were pelleted, phage and packaged plasmid DNA were harvested, and single-stranded DNA was prepared as described by Anderson, Nucl. Acids. Res., 9: 3015 (1981).

b) Site-directed in vitro Mutagenesis

Mutagenesis on p7-1H was carried out using the oligodeoxyribonucleotide, 5-CAGCAGGCCCT-GAATTCTCAG-3', essentially as described by Zoller et al., *Meth. Enzymol.*, 100: 468 (1983), except that the mutant, with the mutation Tyr67→Asn67, was identified by colony hybridization rather than plaque hybridization. Mutations were verified by DNA sequencing directly on the single-stranded plasmid DNA using the dideoxynucleotide chain termination method (Sanger et al., *Proc. Natl. Acad. Sci.* (U.S.A.) 74: 5463 (1977)).

3. Expression and Purification a) Plasmid Preparation

Transformed cells were grown to saturation in 500-ml LB broth containing 50 µg/ml carbenicillin. Cells were pelleted by centrifugation and resuspended in 40 ml of 50mM glucose, 10mM EDTA, 25 mM Tris-HCl (pH 8.0). To this suspension was added 60 ml of 1% sodium dodecyl sulfate, 0.07 M NaOH, and the mixture was incubated for 2 min at 25° C., then at 10 min. at 0° C. To this 52 ml of 4 M acetic acid, 3 M sodium acetate was added and the mixture was incubated for 30 min. at 0° C. This was then centrifuged at 11,500 rpm for 20 min., the supernatant mixed with two volumes of 100% cold ethanol, and the resulting precipitate harvested by centrifugation. The pellet, containing plasmid DNA and RNA, was dried and redissolved in 100 mM Tris (pH 8.0), 10 mM EDTA, 1 µg/ml RNase A. After the resulting solution was clarified by centrifugation, it was adjusted to 0.5 mg/ml in ethidium bromide and an equal weight of CsCl was added. The DNA was then centrifuged in a Beckman VTI65 rotor for 16 hours at 55,000 rpm at 18° C. The DNA band was harvested by side puncture, extracted with n-butanol to remove the ethidium bromide, diluted with $H_2O$, and precipitated by ethanol. DNA was redissolved in 10 mM Tris (pH 8.0), 1 mM EDTA, to a final concentration of 1 mg/ml.

b) Transfection and Expression 293 cells were grown to confluence. Ten µg of t-PA mutant plasmid DNA was mixed with 1 µg of DNA encoding the VA RNA gene (Thimmappaya et al., *Cell*, 31: 543 (1982)) and dissolved in 500 µl of 1 mM Tris-HCl, 0.1 mM EDTA, 0.227 M $CaCl_2$. Added to this (dropwise while vortexing) was 500 µl of 50 mM HEPES (pH 7.35), 280 mM NaCl, 1.5 mM $NaPO_4$, and the precipitate was allowed to form for 10 min. at 25° C. The suspended precipitate was then added to the cells (in 100 mM plate) and allowed to settle for four hours in the incubator. The medium was then aspirated off and 2 ml of 20% glycerol in phosphate-buffered saline was added for 30 sec. The cells were washed twice with 5 ml of serum-free medium, then fresh medium was added and the cells were incubated for five days.

For the creation of stable CHO cell lines expressing the t-PA variant, the BglII/ApaI fragment containing the bulk of the t-PA coding sequences was ligated to the 6.0-kb BglII/ApaI fragments from the vector pPADHFR-6 (described in EPO Pat. Publn. No. 93,619). The resultant plasmid was then introduced into CHO cells and induced to over-express the t-PA variant by amplifying the coding sequence by means of selection in methotrexate-containing media.

c) Purification

Purification of the t-PA product was accomplished by passing the conditioned medium over a column (1-ml bed volume) of controlled pore glass beads to which an anti-t-PA goat polyclonal A6 antibody (prepared according to standard methods known per se) had been coupled. Before the medium was loaded, the column was equilibrated with phosphate-buffered saline and, after loading, the column was equilibrated with 0.1 M Tris-HCl (pH 7.5), 1 M NaCl. The t-PA was eluted with 0.1 M acetic acid, 0.15 M NaCl, 0.02 M arginine, 0.01% Tween 80 (pH 2.0), and fractions were immediately neutralized with Tris-base. Fractions were adjusted to 0.01% Tween 80 before pooling.

B. Biological and Pharmacokinetic Assays 1. t-PA Quantitation

Protein concentrations were routinely determined by an ELISA standardized to native-sequence t-PA (See EPO Pat. Publ. 93,619, supra). Protein purity and homogeneity were analyzed by polyacrylamide gel electrophoresis in the presence of sodium dodecyl sulfate (PAGE-SDS) with the buffer system of Laemmli, *Nature*, 227: 680 (1970). Typically, 7 to 17% gradient gels were used and proteins were visualized with the silver-staining technique of Morrissey, *Anal. Biochem.*, 117: 307 (1981). The N67 t-PA variant prepared as described above was found to be pure and homogeneous by this method.

2. S-2251 Assay

The ability of t-PA to activate plasminogen can be measured in an in vitro assay by preincubating t-PA and plasminogen and then adding the plasmin-specific substrate H-D-valyl-H-leucyl-H-lysine-p-nitronilide (S-2251). The maximum rate of this reaction is observed in the presence of fibrin(ogen) or fragments of fibrin(ogen) that act as stimulators of the reaction.

The plasmin-specific substrate S-2251 was used in a two-stage assay to measure the ability of the sample to activate plasminogen. Fibrinogen could be used as a stimulator by incubating the sample with 0.02 ml of a 20 mg/ml fibrinogen solution in a total volume of 0.12 ml of 0.05 M Tris-HCl, 0.12 M NaCl, 0.01% Tween 80, pH 7.4.

Glu-plasminogen solution (commercially available), 0.03 ml of a 2.0 mg/ml solution in 0.05M Tris, 0.12 M NaCl buffer, pH 8, was then added. After ten min. at 37° C., 0.35 ml of 0.86 mM S-2251 in 0.037 M Tris, 0.086 NaCl, 0.007% Tween 80, pH 7.4 was added. This mixture was incubated for five minutes; then the reaction was stopped by the addition of 0.1 ml of 50% glacial acetic acid. Absorbance at 405 nm was measured. The activity was expressed as the change in absorbance per nanogram per minute in the presence of substrate.

Figure 7:
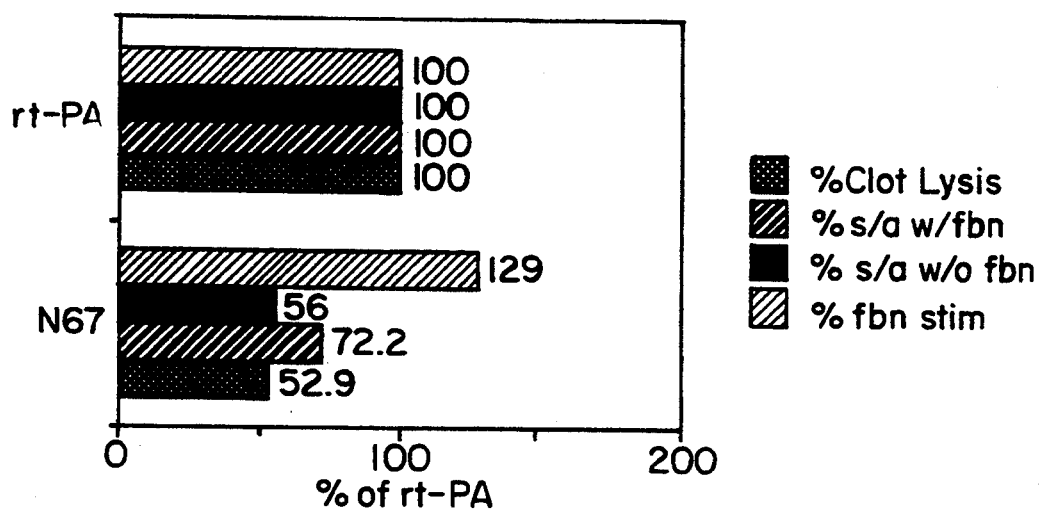
FIG. 7 shows in vitro clot lysis results and S-2251 results, expressed as a percent of native specific activity, for rt-PA and glycosylated N67 t-PA. Results show averages of several independent observations (clot lysis, four determinations; S-2251, two determinations). All were from material expressed transiently in 293 cells and quantified by ELISA.

The assay was run as described, along with an additional set of samples that did not contain fibrinogen. The stimulation is the ratio of the specific activity of the sample containing fibrinogen to the specific activity of the sample not containing fibrinogen. The results, along with clot lysis, are shown in FIG. 7 for both rt-PA and N67 t-PA. Because the specific activity in vitro of the N67 t-PA appears to be compromised more significantly in the absence of fibrinogen, the percent fibrinogen stimulation (which reflects the ratio of the activity in the presence of fibrinogen to the activity in the absence of fibrinogen) is slightly increased over the wild-type rt-PA.

3. Clot Lysis

Wild-type and N67 t-PA were assayed for their ability to lyse fibrin in the presence of saturating concentrations of plasminogen, according to the method of Carlsen et al., *Anal. Biochem*, 168: 428 (1988). The in vitro clot lysis assay measures the activity of tissue plasminogen activators by turbidimetry using a microcentrifugal analyzer. A mixture of thrombin and t-PA test samples is centrifuged into a mixture of fibrinogen and plasminogen to initiate clot formation and subsequent clot dissolution. The resultant profile of absorbance versus time is analyzed to determine the assay endpoint. Activities of the t-PA variants were compared to a standard curve of rt-PA (EPO Publ. No. 93,619, supra). The buffer used throughout the assay was 0.06 M sodium phosphate, pH 7.4, containing 0.01% (v/v) Tween 80 and 0.01% (w/v) sodium azide. Human thrombin was at a concentration of 33 units/ml. Fibrinogen (at 2.0 mg/ml clottable protein) was chilled on wet ice to precipitate fibronectin and then gravity filtered. Glu-plasminogen was at a concentration of 1 mg/ml. The analyzer chamber temperature is set at 37° C. The loader is set to dispense 20 μl of rt-PA (about 500 ng/ml to 1.5 μg/ml) as the sample for the standard curve, or 20 μl of variant rt-PA at a concentration to cause lysis within the range of the standard curve. Twenty μl of thrombin was used as the secondary reagent, and 200 μl of a 50:1 (v/v) fibrinogen: plasminogen mixture as the primary reagent. The absorbance/time program was used with a five-minute incubation time, 340-μm filter, and 90-interval readings.

The results, shown in FIG. 7, indicate that the N67 variant has about 53% of the clot lysis specific activity of normal wild-type t-PA.

4. Fibrin Binding

The method for fibrin binding is a modification of the method described by Rijken et al., *J. Biol. Chem.*, 257: 2920 (1982). The t-PA sample to be tested is added to a solution containing 0.05 M Tris (pH 7.4), 0.12 M NaCl, 0.01% Tween 80, 1 mg/ml human serum albumin, and various concentrations of plasminogen-free fibrin (0, 0.05, 0.1, 0.25, and 0.5 mg/ml). The final volume of the reaction mixture was 1 ml. The sample was incubated at 37° C. for 5 min., followed by the addition of 1 unit of thrombin. The samples were then incubated for one hour at 37° C. The clot was removed by centrifugation, and the amount of t-PA remaining unbound in the supernatant was determined by ELISA.

Figure 8:
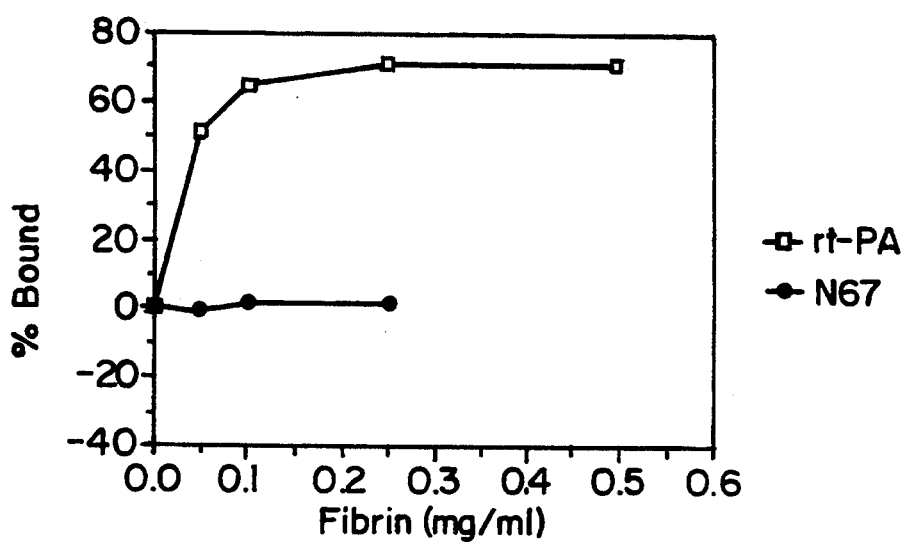
FIG. 8 shows fibrin binding of rt-PA and glycosylated N67 t-PA at a t-PA concentration of 10 ng/ml. Both were expressed transiently in 293 cells.

The data, shown in FIG. 8, are plotted as percent t-PA variant bound versus the fibrin(ogen) concentrations for both N67 t-PA and rt-PA. The results indicate that the N67 t-PA does not bind to fibrin under the assay conditions employed.

5. Verification of Glycosylation

Figure 9A:
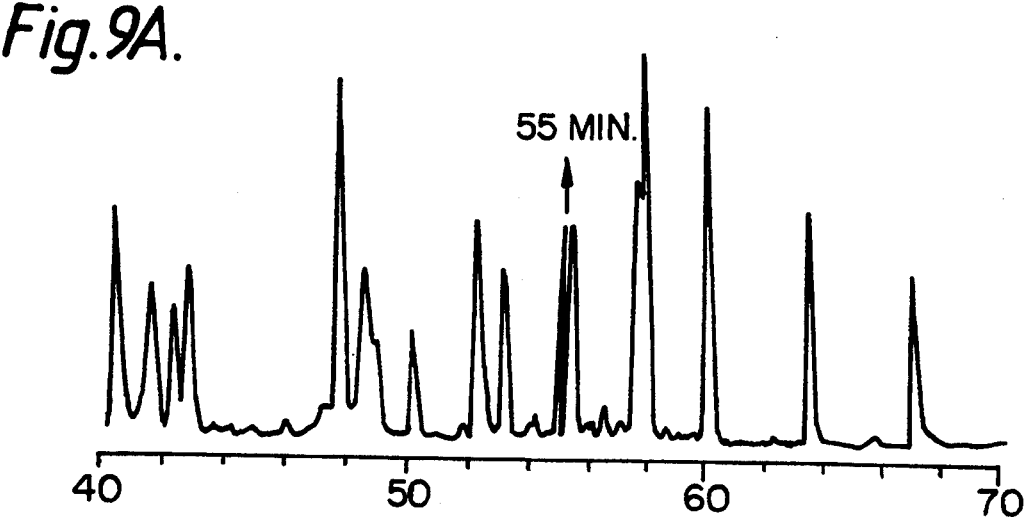
FIGS. 9A–9C show the reverse phase HPLC profiles of tryptic mapping analysis of reduced and carboxymethylated rt-PA, N67 tPA, and N-glycanase-treated (deglycosylated) N67 tPA, respectively. All were expressed transiently in 293 cells.
Figure 9B:
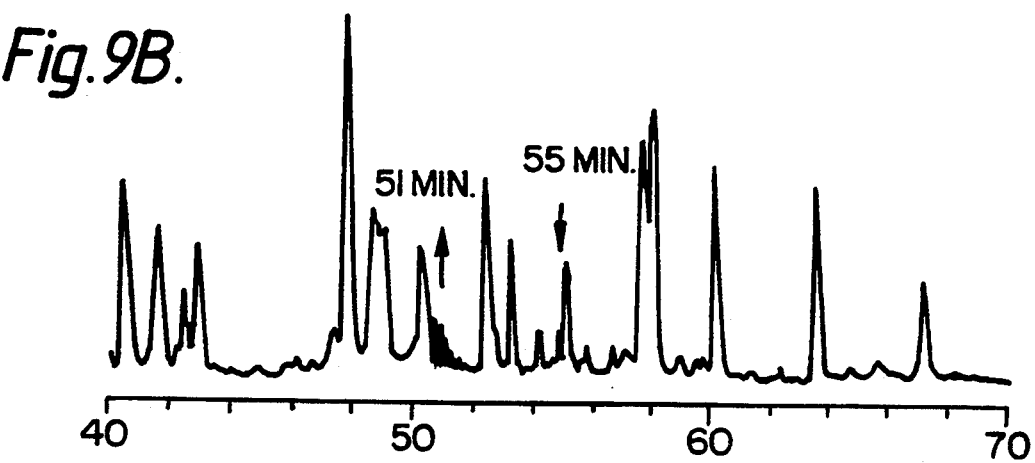
Figure 9C:
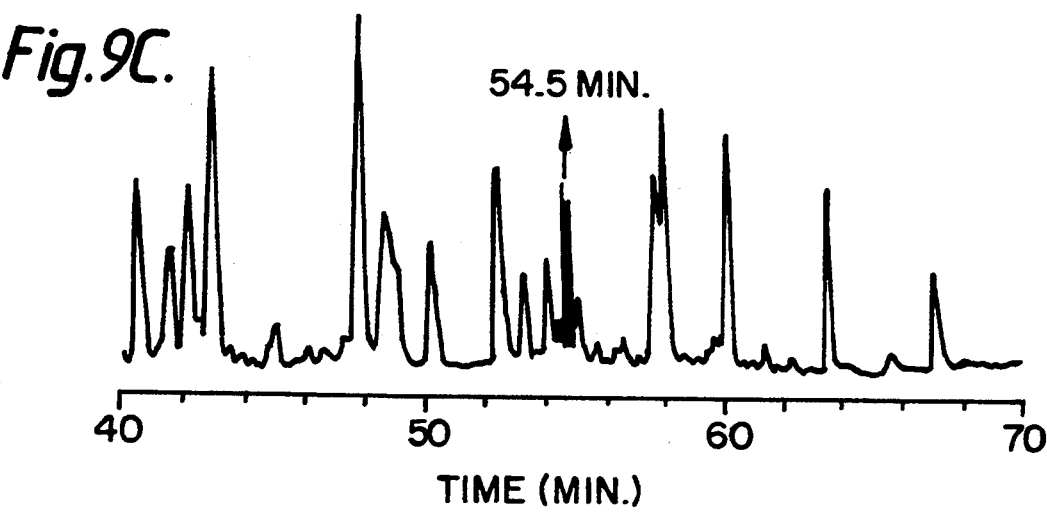

The determination of extra glycosylation at asparagine 67 was done by a tryptic mapping method that utilizes high performance liquid chromatography (HPLC) to resolve a mixture of tryptic peptides into individual components or peaks, whose identities and composition are known. The addition of carbohydrate to a peptide causes an increase in hydrophilicity of that peptide and consequently a change in the HPLC profile (i.e., earlier elution). Individual chromatographic peaks containing the isolated peptide were collected and subjected to amino acid analysis to confirm the identity of the peptide and presence of carbohydrate.

a. Sample Preparation. The method of sample preparation for tryptic mapping was a modification of Crestfield, Stein and Moore, *J. Biol. Chem.*, 238: 622 (1963). The protein samples to be analyzed (1.0 mg each) were dialyzed overnight into 8 M urea, 0.5 M Tris at pH 8.6 with 2 mM EDTA. The samples were reduced with 10 mM dithiothreitol (Sigma Chemical Co.) for 2 hours at 25° C., then S-carboxymethylated with 25 mM iodoacetic acid (Sigma Chemical Co.) at 25° C. in the dark. After 30 minutes the alkylation reaction was quenched by the addition of 20mM dithlothreitol; then the reduced and carboxymethylated (RCM) samples were dialyzed overnight in 100 mM ammonium bicarbonate at pH 8.3 using dialysis tubing with a 3500 molecular weight cut-off.

b. Treatment with N-Glycosidase F. Reduced and carboxymethylated rt-PA was deglycosylated with N-Glycosidase F (Genzyme Corp.) before trypsin digestion. An aliquot (0.4 mg) of reduced and carboxymethylated rt-PA was reconstituted in 0.08 mL of 250 mM sodium phosphate pH 8.6 containing 10 mM EDTA and 0.02 percent sodium azide. N-Glycosidase F (5.0 Manufacturer's Units in 0.018 mL of 50 percent glycerol) was added to the sample, which was then incubated overnight at 37° C. The sample was diluted to 0.4 mL with water and dialyzed against 100 mM ammonium bicarbonate prior to trypsin digestion.

c. Tryptic Digestion. RCM rt-PA was digested in 0.1 M ammonium bicarbonate at ambient temperature with an addition of [L-(tosylamido-2-phenyl)ethylchloromethylketone] (TPCK)-treated trypsin (Cooper Biomedical) at an enzyme-to-substrate ratio of 1:100 (w/w), followed by a second addition of 1:100 after eight hours. The digestions were stopped after 24 hours by freezing (−70° C.).

d. Chromatography. The HPLC separations were performed with a Hewlett-Packard 1090 M liquid chromatograph using a 0.4×15 cm Nova PAK, 5 micron, C-18 reverse phase column (Waters, Inc.). The elution profile was monitored for dual wavelength detection at 214 and 280 nanometers. A trifluoroacetic acid (TFA) solvent system was used, employing 0.1 percent TFA (Pierce Chemical) with a linear gradient of 0.08 percent TFA in acetonitrile (Burdick & Jackson) at a rate of 0.5 percent per minute for 50 minutes, followed by a 1.0 percent per minute linear gradient for 35 minutes at a flow rate of 1.0 milliliters per minute.

e. Amino Acid Analysis. Peptide peaks collected from HPLC were characterized by amino acid analysis after acid hydrolysis. Hydrolysis was performed by incubation of the peptides in constant boiling HCl for 20 hours at 110° C. in vacuo. Analysis of the acid hydrolyzates was accomplished with a Beckman 6300 amino acid analyzer.

f. Results. In FIG. 9, the HPLC profiles of tryptic digests are shown for wild-type RCM rt-PA, N67 mutant RCM t-PA and N-glycanase-treated N67 mutant RCM t-PA in FIGS. 9A, 9B, and 9C, respectively. All samples were produced by transient expression in 293 human kidney cells. The elution profiles seen in FIGS. 9A–9C are taken from that segment of the gradient where tryptic peptide (56–82) is found to elute for wild-type tPA. This peptide (56–82) eluted as a partially resolved doublet at 55 minutes as indicated by the arrow in FIG. 9A.

The N67 tPA mutant was examined in similar fashion (FIG. 9B) and was shown to have lost the wild-type tryptic peptide (56–82) that had eluted at 55 minutes. There appeared a corresponding increase in a broad peak at 51 minutes as shoulder on a pre-existing peak (50.5 minutes). The new peak at 51 minutes was collected, acid hydrolyzed, and quantitated by amino acid analysis. The analysis indicated the presence of aminosugar containing peptide, which was consistent with the earlier elution of glycosylated peptide (56–82).

For confirmation of the glycosylation of the (56–82) tryptic peptide, the RCM N67 t-PA mutant was treated with N-glycosidase to remove N-linked carbohydrate moieties. The tryptic digest of the glycanase-treated mutant protein was analyzed by reverse phase HPLC (FIG. 9C). The earlier eluting shoulder at 51 minutes disappeared with N-glycanase treatment and a new peak at 54.5 minutes appeared in the tryptic map. The slightly earlier elution of N67 (56–82) at 54.5 minutes compared to the wild-type tryptic peptide (56–82) at 55 minutes was consistent with the substitution of tyrosine for aspartic acid (Guo et al., J. Chrom., 359: 499–517, (1986)). (Although the N67 mutant contains carbohydrate linked to asparagine, after N-glycanase treatment the asparagine is converted to an aspartic acid residue.) The assignment of the peak in FIG. 9C at 54.5 minutes as peptide (56–82) was confirmed by amino acid analysis. As seen in Table I the observed amino acid composition follows closely the expected composition, confirming the substitution of tyrosine for asparagine and the N-linked glycosylation of that residue at position 67.

TABLE I

Amino Acid Composition of De-glycosylated Tryptic Peptide (N67: 56–82)

| Amino Acid | Expected | Observed |
|---|---|---|
| Carboxymethyl Cysteine[a] | 4 | 3.4 |
| Aspartate/Asparagine | 3 | 3.0 |
| Threonine | 1 | 1.0 |
| Glutamate/Glutamine | 4 | 4.0 |
| Proline/Cysteic acid[a] | 1 | 1.3 |
| Glycine | 4 | 3.8 |
| Alanine | 2 | 2.1 |
| Half-Cystine[a] | 0 | 0.2 |
| Valine | 1 | 1.1 |
| Methionine | 0 | 0.1 |
| Isoleucine | 0 | 0.3 |
| Leucine | 1 | 1.4 |
| Tyrosine | 0 | 0.1 |
| Phenylalanine | 4 | 3.8 |
| Histidine | 0 | 0.2 |
| Lysine | 1 | 1.0 |
| Arginine | 0 | 0.2 |

[a]The values of carboxymethylated cysteine, cysteic acid and half cystine add to 3.9 compared to the expected value of 4.0.

6. Pharmacokinetics

Twenty rabbits were assigned randomly to one of two treatment groups: rt-PA and glycosylated N67 t-PA. The proteins were labeled with $^{125}$I to approximately 10 μCi/μg and mixed with 0.1 mg/kg rt-PA to decrease nonspecific adsorption of the labeled protein. The dose of trichloroacetic acid (TCA) precipitable $^{125}$I-protein was nominally 5 μCi/kg.

The rabbits had a catheter with a heparin lock in each ear. The dose was administered as an IV bolus in one catheter, followed by a saline flush. All blood samples were obtained from the opposite ear. One ml blood samples were obtained at the following times: 0 (before the dose) and 2, 5, 15, 30, 45, 60, 75, 90, 120, 150, and 180 minutes after the dose. Saline was used to flush the catheters and replace blood volume at each time point. The blood samples were put into 1.5-ml Eppendorf tubes containing 4.2 mM EDTA and 1 mM PPACK (a peptide of phenylalanine-proline-arginine-chloromethyl ketone). The tubes were maintained on ice until centrifuged. After centrifugation, the plasma was removed immediately, placed in Eppendorf tubes, and stored on ice until the end of the study. Proteins in 100 μl of each plasma sample were precipitated with TCA. The $^{125}$I that was bound to proteins was quantified by counting the gamma emissions of each precipitate. The results were based on CPM/100 μl of sample and converted to CPM/ml for data analysis.

The area under the curve (AUC) for each rabbit was computed from 2 to 180 minutes by the trapezoid method using the AUC procedure. Clearance was calculated from the formula CL=Dose/AUC.

The ranking of terminal half-lives for the $^{125}$I-labeled proteins is as follows: rt-PA, N67 t-PA. The actual half-life values must be determined from pharmacokinetic studies with unlabeled proteins. FIG. 10 shows the plots of CPM/ml versus minutes (normalized by dose) for rt-PA and glycosylated N67 t-PA, as well as for des 1–44 t-PA, des 1–44E275 t-PA, and des 1–44E275D184 t-PA, for comparison.

The N67 t-PA was cleared more slowly than the wild-type rt-PA from plasma. The ratio of the clearance of the N67 t-PA to wild-type rt-PA was 0.63. Consequently, at equal infusion rates one would have a 1.6-fold higher plasma concentration with the N67 t-PA compared to wild-type t-PA.

EXAMPLE II

1. Construction of pRK7-t-PA

Plasmid pRK7 was used as the vector for generation of the t-PA mutants. This plasmid, described in EP 278,776 published Aug. 17, 1988, is identical to pRK5 (EP publication number 307,247 published Mar. 15, 1989), except that the order of the endonuclease restriction sites in the polylinker region between Cla I and Hind III is reversed. The t-PA cDNA (Pennica et al., Nature, 301: 214 (1983)) was prepared for insertion into the vector by cutting with restriction endonuclease Bind III (which cuts 49 base pairs 5' of the ATG start codon) and restriction endonuclease Bal I (which cuts 276 base pairs downstream of the TGA stop codon). This cDNA was ligated into pRK7 previously cut with Hind III and Sma I using standard ligation methodology (Maniatis et al., Molecular Cloning: A Laboratory Manual, Cold Spring Harbor Laboratory, New York, 1982). This construct was named pRK7-t-PA.

2. Site-Directed Mutagenesis of pRK7-t-PA

Site-directed mutagenesis of t-PA cDNA was performed by the method of Taylor et al., Nucl. Acids Res., 13: 8765 (1985) using a kit purchased from the Amersham Corporation (catalog number RPN 1253). For generation of the desired mutants, oligonucleotides of sequences coding for the desired amino acid substitutions were synthesized and used as primers. The oligonucleotides used were:

| Variant | Oligonucleotide |
|---|---|
| N9 | 5'CTGCGTTTTGTTATCTCTGCAGAT |
| N18 | 5'CCATGACTGATTTTGCTGGTATAT |
| S39 | 5'CTGTGCCCTGGAACTGTTGCACCA |
| N50 | 5'CTCGCTGCAATTTTTGACAGGCAC |
| S60 | 5'CTGGCAGGTGGACCCGTTGAAACA |
| N96, S98 | 5'CCTGTAGCTGGAGCCGTTGTCCTCGTAGCA |
| N103 | 5'TGTGCTCCAATTGCCCCTGTAGCT |
| N162 | 5'TGAGCTGTAATTCCCCGCCTTAAA |
| N191 | 5'GAGGCTGTGATTGCCACGGTAGGC |
| S207 | 5'TATCAGGATCGAGGAATTCCACGG |
| N298 | 5'GGGCGACCTATTGTGCTTGGCAAA |

Each oligonucleotide was annealed to single-stranded pRK7-tPA that had been prepared by standard procedures (Viera et al., Meth. Enz., 143: 3 (1987)). A mixture of three deoxyribonucleotide triphosphate deoxyriboadenosine triphosphate (dATP), deoxyriboguanosine triphosphate(dGTP), and deoxyribothymidine triphosphate (dTTP), was combined with a modified thiodeoxyribocytosine triphosphate (aS) called dCTP which was provided in the Amersham kit. This mixture of deoxynucleotide triphosphate was added to the plasmid/oligonucleotide complex.

Upon addition of DNA polymerase to this mixture, a strand of DNA identical to pRK7-t-PA except for the mutated bases was generated. In addition, this new strand of DNA contained dCTP(aS) instead of dCTP, which served to protect it from restriction endonuclease digestion. After the template strand of the double-stranded heteroduplex was nicked with an appropriate restriction enzyme, the template strand was digested with Exo III nuclease past the region that contained the mutagenic oligomer. The reaction was then stopped to leave a molecule that was only partially single-stranded. A complete double-stranded DNA homoduplex molecule was then formed by DNA polymerase in the presence of all four deoxyribonucleotide triphosphates, ATP, and DNA ligase.

3. Bacterial Transformation and DNA Preparation

The t-PA variant constructs generated using the protocol above were transformed into *E. coli* host strain MM294tonA using the standard $CaCl_2$ procedure (Maniatis et al., supra) for preparation and transformation of competent cells. The *E. coli* MM294tonA cell line, which is resistant to T1 phage, was prepared by the incision and subsequent imprecise excision of a In10 transposon into the tonA gene. This gene was then inserted, using transposon insertion mutagenesis (Kleckner et al., *J. Mol. Biol.*, 116: 125–159 (1977)), into *E. coli* host MM294 (ATCC 31,446).

DNA was extracted from individual colonies of bacterial transformants using the standard minipreparation procedure of Maniatis et al., supra. The plasmids were further purified by passage through a Sepharose CL6B spin column, and then analyzed by DNA sequencing and by restriction endonuclease digestion and agarose gel electrophoresis.

4. Transfection of Human Embryonic Kidney. 293Cells

Human embryonic kidney 293 cells (ATCC No. CRL 1573) were grown to 70% confluence in 6-well plates. A total of 2.5 μg of t-PA variant DNA was dissolved in 150 μl of 1 mM Tris-HCl, 0.1 mM EDTA, and 0.227 M $CaCl_2$. Added to this (dropwise while vortexing) was 150 μl of 50 mM HEPES buffer (pH 7.35), 280 mM NaCl, and 1.5 mM $NaPO_4$, and the precipitate was allowed to form for twenty minutes at 25° C. The suspended precipitate was then added to the cells in the individual wells in a 6-well plate and allowed to settle for four hours in the incubator. The medium was then aspirated off and 1 ml of 20% glycerol in PBS was added. After 30 seconds, this solution was aspirated off. Three volumes of media containing plasminogen-depleted serum (obtained by removing plasminogen from human serum by conventional procedures) was added to wash the cells, and this solution was then removed. The cells were then placed in fresh media containing the same serum overnight. The next day, the cells were rinsed in PBS and then placed inappropriate growth media. After six days, the media was collected and assayed.

If large-scale purification of the variants is required for production in significant quantities, a useful transfection procedure is described in *Current Protocols in Molecular Biology*, Ausubel et al., eds. (Wiley Interscience, 1988) and modified slightly as follows: A suspension of human embryonic kidney 293 cells is grown in a cell culture medium and concentrated by pelleting. The pellet is resuspended to a concentration of about $10^8$ cells per milliliter and the cells are washed as necessary in serum-free media. The DNA-dextran solution is added at a concentration of about 250 μg of DNA per 500 ml of cells, and this mixture is incubated with mild agitation at 37° C. for up to 90 minutes. DMSO is added to a final concentration of ten percent and, after about two minutes, fresh medium is added to dilute the cells to about $10^6$ per milliliter. Cells are then incubated for up to seven days, after which time the supernatant is collected.

Purification of these variants maybe accomplished by passage of the supernatant over a column of glass beads coupled to anti-t-PA goat polyclonal A6 antibody. The column is preconditioned with PBS. After the supernatant is loaded, the column is equilibrated with a Tris-saline buffer [0.1M Tris.HCl (pH 7.5) and 1M NaCl]. The t-PA variant is then eluted with 0.1M acetic acid, 0.15 M NaCl, 0.02 M arginine, and 0.01% Tween 80. Fractions are immediately neutralized with Tris base and adjusted to 0.01% Tween 80.

05. Biological Assays

A. t-PA Quantitation

The amount of t-PA present in the cell culture supernatants was determined by the ELISA procedure using polyclonal antibodies prepared against wild-type t-PA. All of the t-PA variants prepared were found to be pure and homogeneous by this method.

B. S-2288 Assay

The S-2288 assay was used to measure the proteolytic activity of the mutants in both the one- and two-chain forms. The S-2288 substrate consists of a small peptide linked to a paranitroanilide chromophore. t-PA cleaves the bond between the small peptide and the chromophore.

Standard curve samples were prepared by diluting wild-type rt-PA (recombinant t-PA) with cell culture media. The standard curve samples and rt-PA mutant samples were added to the wells of a microtiter plate. If the assay was used to measure the activity of two-chain rt-PA, an incubation step with human plasmin was included in the procedure. Human plasmin (KabiVitrum) was added to a final concentration of 0.13 CU (casein units)/ml. The samples were incubated for 90 minutes at room temperature. For assaying the samples in the single-chain form, the plasmin solution was replaced by PBS and the 90-minute incubation was omitted.

Aprotinin (Sigma, approximately 14 TIU (trypsin inhibitor units)/mg) was added to a final concentration of 72 μg/ml to inhibit the plasmin activity, and the samples were incubated at room temperature for 15 minutes. A 2.16mM solution of S-2288 was diluted to 1.45 mM with 0.1 M Tris, 0.106 mM NaCl, 0.02% sodium azide, pH 8.4, and 100 μl of this solution was added to each well of the microtiter plate (final volume in each well was 200 μl). Color development was monitored at 405 nm. The slope of the absorbance versus time curve for each sample and standard was determined. A standard curve was prepared by plotting the slope of the absorbance versus time curve as a function of rt-PA concentration for the rt-PA standards. The relative activity concentration of the mutants was then determined from the standard curve. The activity concentration of each mutant was divided by the concentration for the mutant obtained in the rt-PA ELISA, and the resulting specific activities were expressed relative to wild-type t-PA, which was assigned a value of 1.0.

C. S-2251 Assay

This assay is an indirect assay for t-PA activity. In this assay, plasminogen is converted to plasmin by the action of t-PA, and plasmin cleaves the S-2251 substrate to release the paranitroanilide chromophore. Production of this chromophore is then measured over time.

1. Fibrin-Stimulated S-2251 Assay

Standard curve samples were prepared as described for the S-2288 assay. Samples assayed in the two-chain form were incubated with plasmin-Sepharose. Plasmin-Sepharose was prepared by coupling approximately 20.8 CU of human plasmin (KabiVitrum) to 1 ml of cyanogen bromide activated Sepharose (Pharmacia). The plasmin-Sepharose (50 μl of a 5% slurry) was incubated with shaking for 90 minutes at room temperature with 150 μl of sample. Following the incubation, the resin was removed by centrifugation, and 10 μl of sample were added to the wells of a microtiter plate.

For samples assayed in the one-chain form, 50 μl of cell culture media were added in place of resin, and the incubation step was omitted. Human thrombin (10 μl of a 42 unit/ml solution) was added to each well. The reaction in each well was started by the addition of a cocktail (130 μl) composed of 28 μl of human Glu-plasminogen (5.3μM); 10 μl of plasminogen-free human fibrinogen (10 μM); 30 μl of 3 mM S-2251 (KabiVitrum); and 62 μl of PBS. Color development was monitored at 405 nm, and the absorbance at the reference wavelength of 492 nm was subtracted from each time point. The slope of the absorbance versus time squared curve was determined for each standard and variant sample. A standard curve was prepared by plotting the slope of the absorbance versus time squared curve as a function of rt-PA concentration for the rt-PA standards. The determination of the relative specific activity for the variants was as described for the S-2288 assay.

2. Fibrinogen-Stimulated S-2251 Assay

This assay was performed as described for the fibrin-stimulated S-2251 assay except that PBS was substituted for the thrombin and no reference wavelength was used.

3. Plasma Clot S-2251 Assay

The standard curve sample preparation and the conversion of one-chain rt-PA to two-chain rt-PA using plasmin-Sepharose were as described for the fibrin-stimulated S-2251 assay. Human thrombin (10 μl of a 31 μg/ml solution) was added to each well of the microtiter plate. The standard and variant samples (40 μl) were added to the plate and the reaction was started by adding 100 μl of a mixture of 90 μl of acid citrate dextrose human plasma and 10 μl of 9.1 mM S-2251 (KabiVitrum). Color development was monitored at 405 nm and the absorbance at the reference wavelength of 492 nm was subtracted from each time point. The analysis of the data was as described for the fibrin-stimulated S-2251 assay.

4. Plasma S-2251 Assay

This assay was performed as described for the plasma clot S-2251 assay except that PBS was substituted for the thrombin and no reference wavelength was used.

The results of the S-2288 and S-2251 assays are provided in Table II.

TABLE II

| | A | B | C | D | E | F | G | H |
|---|---|---|---|---|---|---|---|---|
| 1 | ID | Mutation | | | | | Activity Relative to wt rt-PA (where wt is 1.0) | |
| 2 | | | | | | | | |
| 3 | | | | S-2288 | S-2288 | Unstimulated | Fibrinogen | Fibrin |
| 4 | | | | 2 Chain | 1 Chain | S-2251 | Stimulated | Stimulated |
| 5 | | | | | | 2 Chain | S-2251 | S-2251 |
| 6 | | | | | | | 2 Chain | 2 Chain |
| 7 | | | | | | | | |
| 8 | 1G12317 | N9 | | 0.76 | 0.89 | 0.76 | 0.69 | 0.80 |
| 9 | | | | | | | | |
| 10 | 1Y12318 | N18 | | 0.73 | 0.85 | 0.54 | 0.69 | 0.88 |
| 11 | | | | | | | | |
| 12 | 1G12319 | S39 | | 0.72 | 0.79 | 0.32 | 0.41 | 0.71 |
| 13 | | | | | | | | |
| 14 | 1Y12320 | N50 | | 0.78 | 0.85 | 0.45 | 0.51 | 0.70 |
| 15 | | | | | | | | |
| 16 | 1B12321 | S60 | | 0.71 | 0.73 | 0.42 | 0.22 | 0.28 |
| 17 | | | | | | | | |
| 18 | B12094 | N67 | | 1.07 | 0.97 | 0.50 | 0.50 | 0.67 |
| 19 | | | | | | | | |
| 20 | 1W12322 | N96, S98 | | 0.78 | 1.05 | 0.73 | 0.68 | 0.78 |
| 21 | | | | | | | | |
| 22 | 1R12323 | N103 | | 0.82 | 0.88 | 0.40 | 0.42 | 0.69 |
| 23 | | | | | | | | |
| 24 | 1G12324 | N162 | | 1.29 | 1.40 | 0.49 | 0.72 | 1.06 |
| 25 | | | | | | | | |
| 26 | 1R12325 | N191 | | 0.90 | 1.05 | 0.52 | 0.68 | 0.88 |
| 27 | | | | | | | | |
| 28 | 1W12326 | S207 | | 0.79 | 0.89 | 0.31 | 0.53 | 0.81 |
| 29 | | | | | | | | |
| 30 | 1G12327 | N298 | | 1.25 | 1.39 | 0.52 | 0.85 | 1.87 |

| | I | J | K | L |
|---|---|---|---|---|
| 1 | Activity Relative to wt rt-PA (where wt is 1.0) | | | |
| 2 | | | | |
| 3 | Fibrin | Plasma | Plasma Clot | Plasma Clot |
| 4 | Stimulated | S-2251 | S-2251 | S-2251 |
| 5 | S-2251 | 2 Chain | 2 Chain | 1 Chain |
| 6 | 1 Chain | | | |
| 7 | | | | |
| 8 | 0.84 | 0.82 | 0.80 | 0.80 |

TABLE II-continued

| | | | | |
|---|---|---|---|---|
| 9 | | | | |
| 10 | 0.90 | 0.78 | 0.88 | 0.87 |
| 11 | | | | |
| 12 | 0.73 | 0.67 | 0.61 | 0.63 |
| 13 | | | | |
| 14 | 0.77 | 0.76 | 0.61 | 0.67 |
| 15 | | | | |
| 16 | 0.29 | 0.58 | 0.19 | 0.18 |
| 17 | | | | |
| 18 | 0.67 | 1.36 | 0.46 | 0.42 |
| 19 | | | | |
| 20 | 0.82 | 0.67 | 0.75 | 0.74 |
| 21 | | | | |
| 22 | 0.74 | 0.67 | 0.60 | 0.64 |
| 23 | | | | |
| 24 | 1.14 | 1.25 | 0.93 | 0.97 |
| 25 | | | | |
| 26 | 0.92 | 0.94 | 0.82 | 0.85 |
| 27 | | | | |
| 28 | 0.80 | 0.92 | 0.77 | 0.81 |
| 29 | | | | |
| 30 | 1.96 | 0.62 | 1.40 | 1.33 |

D. Fibrin Binding

The method for fibrin binding determination employed was essentially the same as that used in Example I. However, the following exceptions were made due to the assay of transiently expressed 293 cell culture supernatants. The assay was conducted on sample volumes of 100 µl or less, in microtiter plates using radiolabeled protein samples obtained by the $^{125}$I YPRck method for labeling of cell culture supernatants as described below under Evaluation of Clearance Rate. The following results were obtained for the variants listed below:

TABLE III

Fibrin Binding Determination

| Variant | Fibrin Binding (normalized to wild-type t-PA) |
|---|---|
| N9 | 1.05 |
| N18 | 1.15 |
| S39 | 0.99 |
| N50 | 0.92 |
| S60 | 0.33 |
| N67 | |
| N96, S98 | 1.00 |
| N103 | 0.89 |
| N162 | 0.82 |
| N191 | 1.00 |
| S207 | 1.00 |
| N298 | 1.11 |
| N387 | ND |

E. Purified Clot and Plasma Clot Lysis Assays

All samples were converted from the one-chain rt-PA to the two-chain rt-PA form using plasmin-Sepharose as described for the fibrin-stimulated S-2251 assay above. The purified clot lysis assay was performed essentially as described by Carlsen et al., supra, but in microtiter plates. The plasma clot lysis assay was performed as follows: 10 µl of 0.15 M calcium chloride was added to microtiter plate wells. Each well then received 90 µl of centrifuged and 0.45-micron-filtered human citrated plasma pool. The contents were thoroughly mixed so as to create the plasma clot. Standard (Activase®t-PA) and samples were diluted in assay buffer (0.1 M NaCl, 0.03 M sodium bicarbonate—added on the day of the experiment, 4 mM KCl, 1 mM calcium chloride, 1 mM dibasic sodium phosphate, 0.3 mM magnesium chloride, 0.4 mM magnesium sulfate, 20 mM HEPES [4-(2-hydroxyethyl)-1-piperazineethane sulfonic acid], and 0.01% Polysorbate 80, pH 7.4) to a concentration of twice their final value (18–800 ng/ml). Individual standards or samples were then mixed with an equal volume of the same plasma pool. A total of 100 µl of the mixture was layered over the plasma clot after the clot had been allowed to sit at ambient temperature for 6–8 hours. Optical density at 405 nm was then read for the whole plate. The plate was then incubated at 37° C. for about 15 hours. The optical density measurement was repeated. For each well, an optical density difference from time of 15 hours to time of 0 hours was obtained by subtraction. For the standards, the optical density difference was plotted as a function of the log of the concentration of the standard. Unknowns were interpolated from the standard curve. Normalization was to identically treated wild-type controls. Standard curves were determined using a four-parameter fit program. The plate reader employed was from SLT-Laboratories, Model EAR340AT (Austria).

The results are shown in Table IV.

TABLE IV

| | A | B | C | D | E | F |
|---|---|---|---|---|---|---|
| 1 | ID | MUTATION | RELATIVE ACTIVITY TO WT RT-TPA*(WHERE WT IS 1.0) | | | |
| 2 | | | purified | | | |
| 3 | | | clot lysis | plasma clot lysis | | |
| 4 | | | | | | |
| 5 | 1G12317 | N9 | 0.69 | 0.8 | | |
| 6 | | | | | | |
| 7 | 1Y12318 | N18 | 0.65 | 0.85 | | |
| 8 | | | | | | |
| 9 | 1G12319 | S39 | 0.52 | 0.47 | | |
| 10 | | | | | | |
| 11 | 1Y12320 | N50 | 0.62 | 0.54 | | |
| 12 | | | | | | |
| 13 | 1B12321 | S60 | 0.24 | 0 | | |
| 14 | | | | | | |

TABLE IV-continued

| A  |        | B       | C    | D    | E | F |
|----|--------|---------|------|------|---|---|
| 15 | B12094 | N67     | 0.76 | 0.26 |   |   |
| 16 |        |         |      |      |   |   |
| 17 | 1W12322| N96, S98| 0.73 | 0.81 |   |   |
| 18 |        |         |      |      |   |   |
| 19 | 1R12323| N103    | 0.57 | 0.69 |   |   |
| 20 |        |         |      |      |   |   |
| 21 | 1G12324| N162    | 0.93 | 0.38 |   |   |
| 22 |        |         |      |      |   |   |
| 23 | 1R12325| N191    | 0.71 | 0.69 |   |   |
| 24 |        |         |      |      |   |   |
| 25 | 1W12326| S207    | 0.67 | 0.84 |   |   |
| 26 |        |         |      |      |   |   |
| 27 | 1G12327| N298    | 0.91 | 1.21 |   |   |
| 28 |        |         |      |      |   |   |

*WT RT-TPA = wild-type recombinant t-PA

6. Evaluation of Clearance Rate

The clearance rate of the t-PA glycosylation variants was assessed by radiolabeling the protein, injecting it into mice, and measuring radioactivity in the blood of the mice over time.

The source of the t-PA protein was the culture media from cell cultures transfected with DNA encoding the desired variants as described above. The protein (in 900 μl of culture medium) was incubated for 30 minutes with the suicide substrate YPRck (try-pro-arg-chloromethylketone custom synthesized by Bachem, Basel, Switzerland) that had been previously iodinated using 125I with chloramine T catalysis of the radioiodination. This substrate binds irreversibly to t-PA and the t-PA therefore becomes radiolabeled. To separate free substrate from substrate bound to t-PA, the solution was passed over a Sephadex G-25 column, and eluted in a solution containing 1 mg/ml gelatin. The eluant was about 2,000,000 cpm per μg t-PA. Approximately 100,000 cpm of labeled t-PA in a volume of 100 μl was injected into each mouse through the tail vein. To determine the clearance rate of each variant, the mice were bled at various times after the injection, and 70 μl of blood was collected. An anti-coagulant was added to each blood sample immediately. A solution of 20% TCA was added to each collected blood sample. The amount of TCA precipitable radioactive counts was measured in a gamma scintillation counter and used to determine the amount of circulating t-PA at that collection time.

Figure 11:
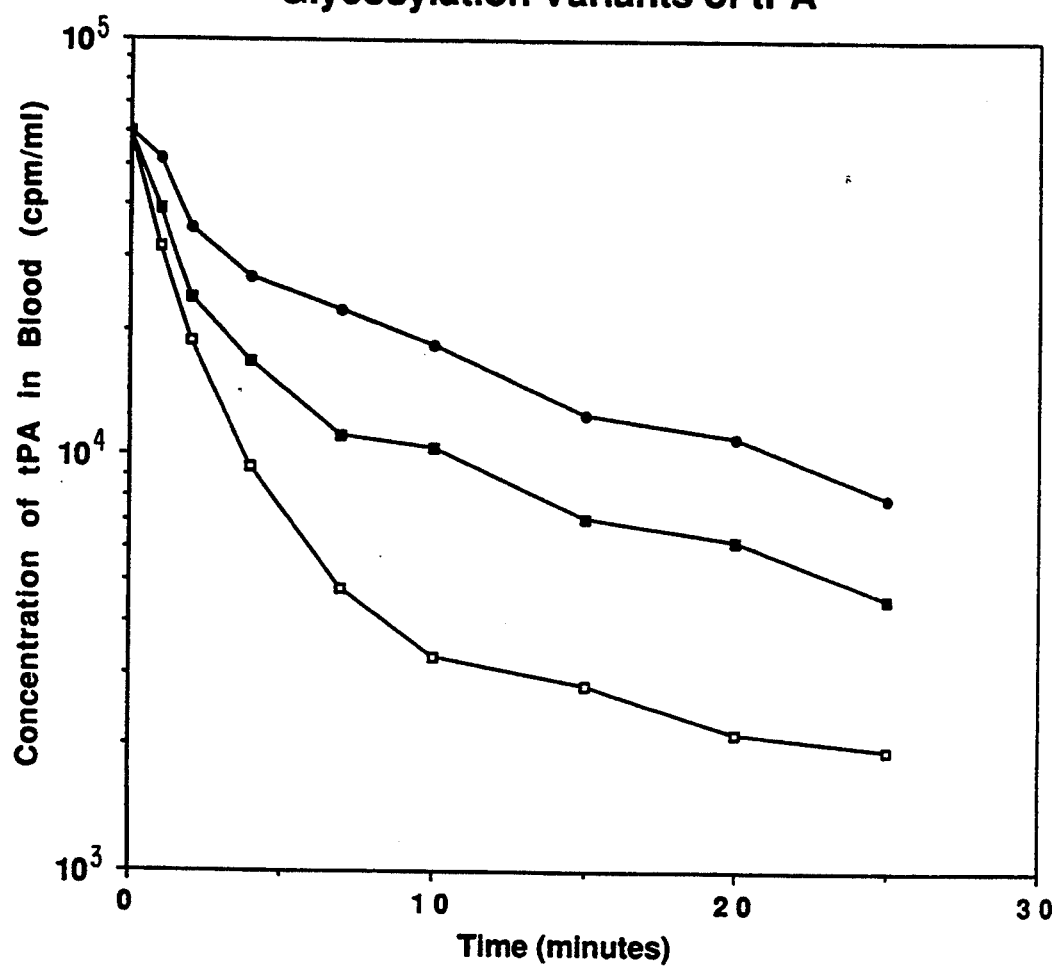
FIG. 11 shows the pharmacokinetic profiles, in mice, of various t-PA variants and wild-type t-PA expressed transiently in 293 cells. The solid circles represent N103, the solid squares represent S60, and the open squares represent wild-type t-PA. The blood volume of the mouse into which the labeled t-PA molecule will distribute (or dilute) was calculated by determining experimentally the initial volume of distribution based on slowly cleared protein with monoexponental decay kinetics, in this case serum albumin.

Four mice were used for each t-PA variant assayed. The mice were divided into two groups, and both mice in a group were bled at the time points listed below. The data from the two groups were then combined and plotted on a graph of time versus cpm in the blood. A plot of two of the variants tested, i.e., S60 and N103, as well as of wild-type t-PA, is shown in FIG. 11. The area under the curve (AUC) for each mouse was computed from 1 to 25 minutes by the trapezoid method using the AUC procedure. Clearance rate was calculated from the formula CL - Dose/AUC. The clearance rates from blood of the variants, normalized to that of wild-type t-PA (clearance rate of wild-type t-PA divided by clearance rate of the variant), are presented in Table IV below.

Group I
Bled at 1, 4, 10, 20, and 30 minutes after injection.
Group II
Bled at 2, 7, 15, 25, and 40 minutes after injection.

TABLE V

| Variant | Mouse Clearance Values* Clearance Rate (normalized to wild-type t-PA) |
|---------|---|
| N9      | 1.02 |
| N18     | 1.00 |
| S39     | 0.84 |
| N50     | 0.88 |
| S60     | 0.49 |
| N67     | 0.58 |
| N96, S98| 0.94 |
| N103    | 0.29 |
| N162    | 1.05 |
| N191    | 1.02 |
| S207    | 1.00 |
| N298    | 1.12 |

*The half-life is inversely proportional to the clearance rate value. Thus, smaller clearance rate values indicate longer plasma half-life.

Of the variants tested, N96, S98, S39, N50, S60, N67, and N103 had slower clearance rates than native t-PA. Thus, these variants fall within the claims. N103 was found to have the slowest clearance rate of this group of variants.

EXAMPLE III

Additional mutants are prepared with the following oligonucleotides, where the underlining indicates where the codon changes were made:

| Variant | Domain | Sequence |
|---------|--------|----------|
| N101    | K1     | 5'CCACGTGCCATTGTAGCTGATGCC |
| N104    | K1     | 5'CGCTGTGCTATTCGTGCCCCTGTA |
| N107    | K1     | 5'GCCACTCTCATTTGTGCTCCACGT |
| N112    | K1     | 5'GTTGGTGCAATTGGCGCCACTCTC |
| N198    | K2     | 5'GCAGGAGGCATTCGACTCGGTGAG |
| A219    | K2     | 5'CTGGGCACTGGCGTTCTGTGCTGT |

-continued

| Variant | Domain | Sequence |
|---|---|---|
| N250 | K2 | 5'CCACGTCAG<u>ATT</u>GCGGTTCTTCAG |
| N99,S101 | K1 | 5'CCACGTGCC<u>GG</u>AGTA<u>ATT</u>GATGCCCTGGTC |
| N105,S107 | K1 | 5'GCCACTCTC<u>GGA</u>TGT<u>ATT</u>CCACGTGCCCCT |
| N106,S108 | K1 | 5'GGCGCCACT<u>GGA</u>CGC<u>ATT</u>GCTCCACGTGCC |
| N109,S111 | K1 | 5'GGTGCACTC<u>GGA</u>GCC<u>ATT</u>CTCCGCTGTGCT |
| N94,S96 | K1 | 5'GCTGATGCC<u>GGA</u>GTC<u>ATT</u>GTAGCACGTGGC |
| N387 | SP | 5'CACGCTGCT<u>ATT</u>CTGGGCACAGCG |

These variants are prepared and assayed as described in Example II.

We claim:

1. A fibrinolytically active human tissue plasminogen activator (t-PA) amino acid sequence variant having one or more amino acid substitutions which provide an Asn-X-Ser or Asn-X-Thr tripeptidyl sequence that starts at an amino acid position selected from the group consisting of amino acid positions 57 to 61, 63 to 69, 99, 101, 103 to 105, 106, 107, 109, 112 and 250 of the amino acid sequence of native human t-PA, wherein X is any amino acid except proline, and having N-linked glycosylation attached to the Asn within such tripeptidyl sequence.

2. The variant of claim 1 that is selected from the group consisting of variants having (1) a serine at position 60 of the native t-PA, (2) an asparagine at position 35 of native t-PA, (3) an asparagine at position 99 and a serine or threonine at position 101 of the native t-PA, (4) an asparagine at position 101 of the native t-PA, (5) an asparagine at position 103 of the native t-PA, (6) an asparagine at position 104 of the native t-PA, (7) an asparagine at position 105 and a serine or threonine at position 107 of the native t-PA, (8) an asparagine at position 106 and a serine or threonine at position 108 of the native t-PA, (9) an asparagine at position 107 of the native t-PA, (10) an asparagine at position 109 and a serine or threonine at position 111 of the native t-PA, (11) an asparagine at position 112 of the native t-PA, and (12) an asparagine at position 250 of the native t-PA.

3. The variant of claim 2 wherein the variant is selected from the group consisting of variants having an asparagine at either amino acid position 67 or 103, or having an asparagine at amino acid position 105 and either a serine or threonine at amino acid position 107 of the native t-PA.

4. The variant of claim 1 further comprising the deletion of amino acids 1–44.

5. The variant of claim 4 which additionally has at least one amino acid at any of amino acid positions 184–186 substituted with another amino acid such that glycosylation cannot occur at amino acid position 184.

6. The variant of claim 4 that is rendered resistant to enzymatic cleavage by an amino acid substitution at position 275 or 277 or both.

7. The variant of claim 6 in which position 275 is substituted by glycine or glutamic acid.

8. The variant of claim 7 in which position 275 is substituted by glutamic acid.

9. The variant of claim 6 wherein position 277 is substituted by an amino acid other than lysine.

10. The variant of claim 9 in which said amino acid is isoleucine.

11. The variant of claim 1 wherein the variant has an additional alteration selected from the group of alterations consisting of alanine substituted at amino acid position(s) 267, 283+287, 296-299, 303-304, 331-332, 339+342, 347-349+351, 364-366, 408, 410, 416-418, 426-427+429-430, 432+434, 440, 445+449, 449+453, 460+462, or 477 of the amino acid sequence of native human t-PA, where "+" indicates the substitution of alanine only at the positions designated, and the "-" indicates the substitution of alanine at the positions designated and all positions therebetween.

12. The variant of claim 1 selected from the group consisting of des 1–44N67E275 t-PA, des 1–44N67D1-84E275 t-PA, des 1–44N67S184E275 t-PA, des 1–44N67K213E275 t-PA, des 1–44N67R2-10A211R212R213E275 t-PA, des 1–44N67R252E275 t-PA, des 1–44N67K210E275 t-PA, des 1–44N67E27-5I277 t-PA, des 1–44N67D184E275I277 t-PA, des 1–44N67S184E275I277 t-PA, des 1–44N67K213E27-5I277 t-PA, des 1–44N67R210A211R212R213E275I277 t-PA, des 1–44N67R252E275I277 t-PA, des 1–44N67K210E275I277 t-PA, N67A267 t-PA, N67A283A287 t-PA, N67A296A297AA298A299 t-PA, N67A303A304 t-PA, N67A331A332 t-PA, N67A33-9A342 t-PA, N67A347A348A349A351 t-PA, N67A36-4A365A366 t-PA, N67A408 t-PA, N67A410 t-PA, N67A416A417A418 t-PA, N67A426A427A429A430 t-PA, N67A432A434 t-PA, N67A440 t-PA, N67A44-5A449 t-PA, N67A449A453 t-PA, N67A460A462 t-PA, N67A477 t-PA, N67N103 t-PA, N60N103 t-PA, N60N67N103 t-PA, des 1–44N103E275 t-PA, des 1–44N103D184E275 t-PA, des 1–44N103S184E275 t-PA, des 1–44N103K213E275 t-PA, des 1–44N103R2-10A211R212R213E275 t-PA, des 1–44N103R252E275 t-PA, des 1–44N103K210E275 t-PA, des 1–44N103E27-5I277 t-PA, des 1–44N103D184E275I277 t-PA, des 1–44N103S184E275I277 t-PA, des 1–44N103K213E27-5I277 t-PA, des 1–44N103R210A211R212R213E27-5I277 t-PA, des 1–44N103R252E275O277 t-PA, des 1–44N103K210E275I277 t-PA, N103A267 t-PA, N103A283A287 t-PA, N103A296A297A298A299 t-PA, N103A303A304 t-PA, N103A331A332 t-PA, N103A339A342 t-PA, N103A347A348A349A351 t-PA, N103A364A365A366 t-PA, N103A408 t-PA, N103A410 t-PA, N103A416A417A418 t-PA, N103A426A427A429A430 t-PA, N103A432A434 t-PA, N103A440 t-PA, N103A445A449 t-PA, N103A44-

9A453 t-PA, N103A460A462 t-PA, and N103A477 t-PA.

13. A composition for treating a vascular disease or condition comprising a therapeutically effective amount of the plasminogen activator variant of claim 1 in admixture with a pharmaceutically acceptable carrier.

14. A method of treating a vascular disease or condition in a patient comprising administering the composition of claim 13 to the patient.

15. A fibrinolytically active tissue plasminogen activator (t-PA) amino acid sequence variant having an asparagine at amino acid position 103 of the native human t-PA, or having an asparagine at amino acid position 105 and a serine or threonine at amino acid position 107 of the native human t-PA, as part of the Asn-X-Ser or Asn-X-Thr tripeptidyl sequence, wherein X is any amino acid except proline.

16. The t-PA variant of claim 15 having alanine substituted at each of amino acid positions 296–299 of the native human t-PA.

17. The t-PA variant of claim 16 which additionally has at least one amino acid selected from the group of amino acid positions 117–119, 184–186, 218–220, and 448–450 substituted with another amino acid such that glycosylation cannot occur at at least one of amino acid positions 117, 184, 218, or 448.

18. The t-PA variant of claim 15 which additionally has at least one amino acid selected from the group of amino acid positions 117–119, 184–186, 218–220, and 448–450 substituted with another amino acid such that glycosylation cannot occur at at least one of amino acid positions 117, 184, 218, or 448.

19. A fibrinolytically active human tissue plasminogen activator (t-PA) variant having an asparagine substituted at amino acid position 103 of the native human t-PA, as part of the Asn-X-Ser or Asn-X-Thr tripeptidyl sequence, wherein X is any amino acid except proline.

20. The t-PA variant of claim 19 having alanine substituted at each of amino acid positions 296–299 of the native human t-PA.

21. The t-PA variant of claim 20 which additionally has at least one amino acid selected from the group of amino acid positions 117–119, 184–186, 218–220, and 448–450 substituted with another amino acid such that glycosylation cannot occur at at least one of amino acid positions 117, 184, 218, or 448.

22. A composition for treating a vascular disease or condition comprising a therapeutically effective amount of t-PA variant of claim 21 in admixture with a pharmaceutically acceptable carrier.

23. A method of treating a vascular disease or condition in a patient comprising administering the composition of claim 22.

24. The t-PA variant of claim 66 which additionally has at least one amino acid selected from the group of amino acid positions 117–119, 184–186, 218–220, and 448–450 substituted with another amino acid such that glycosylation cannot occur at at least one of amino acid positions 117, 184, 218, or 448.

25. A composition for treating a vascular disease condition comprising a therapeutically effective amount of t-PA variant of claim 24 in admixture with a pharmaceutically acceptable carrier.

26. A method of treating a vascular disease or condition in a patient comprising administering the composition of claim 25.

* * * * *

UNITED STATES PATENT AND TRADEMARK OFFICE
CERTIFICATE OF CORRECTION

PATENT NO. : 5,385,732
DATED : January 31, 1995
INVENTOR(S) : Anderson et al.

It is certified that error appears in the above-identified patent and that said Letters Patent is hereby corrected as shown below:

Claim 1,
Line 3, insert -- 67 -- after "asparagine at position".

Claim 24,
Line 1, cancel "claim 66" and replace it with -- claim 19 --.

Signed and Sealed this

Twenty-first Day of August, 2001

*Attest:*

*Attesting Officer*

NICHOLAS P. GODICI
*Acting Director of the United States Patent and Trademark Office*